US012805698B2

(12) United States Patent
Kimura et al.

(10) Patent No.: US 12,805,698 B2
(45) Date of Patent: Nov. 24, 2026

(54) ENDOSCOPE SYSTEM, MEDICAL INFORMATION PROCESSING APPARATUS, MEDICAL INFORMATION PROCESSING METHOD, MEDICAL INFORMATION PROCESSING PROGRAM, AND RECORDING MEDIUM

(71) Applicant: FUJIFILM Corporation, Tokyo (JP)

(72) Inventors: Yuya Kimura, Kanagawa (JP); Yuma Hori, Kanagawa (JP); Tatsuya Kobayashi, Kanagawa (JP); Yuichi Sakaguchi, Kanagawa (JP); Kenichi Harada, Kanagawa (JP); Takeru Sugiyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 249 days.

(21) Appl. No.: 18/582,650

(22) Filed: Feb. 21, 2024

(65) Prior Publication Data

US 2024/0188799 A1 Jun. 13, 2024

Related U.S. Application Data

(63) Continuation of application No. PCT/JP2022/033260, filed on Sep. 5, 2022.

(30) Foreign Application Priority Data

Sep. 8, 2021 (JP) ................................ 2021-146308

(51) Int. Cl.
*G06V 10/70* (2022.01)
*A61B 1/00* (2006.01)
(Continued)

(52) U.S. Cl.
CPC ...... *A61B 1/0004* (2022.02); *A61B 1/000096* (2022.02); *G06T 7/0012* (2013.01);
(Continued)

(58) Field of Classification Search
CPC .. A61B 1/0004; A61B 1/00096; G06V 10/70; G06V 2201/03; G06T 7/0012;
(Continued)

(56) References Cited

U.S. PATENT DOCUMENTS

| | | | | |
|---|---|---|---|---|
| 11,107,571 | B2 | 8/2021 | Kashima et al. | |
| 2008/0133233 | A1 * | 6/2008 | Tsubura | G16H 40/63 704/235 |

(Continued)

FOREIGN PATENT DOCUMENTS

| | | |
|---|---|---|
| JP | H0852105 | 2/1996 |
| JP | 2004102509 | 4/2004 |

(Continued)

OTHER PUBLICATIONS

Kenichi Nakamura, "Real-time observation input system "Voice Capture" with voice recognition for endoscopy", Eizo Joho Industrial, Jan. 1, 2016, with partial English translation thereof, pp. 67-71, vol. 48, No. 1.

(Continued)

*Primary Examiner* — Syed Haider
(74) *Attorney, Agent, or Firm* — JCIPRNET

(57) ABSTRACT

An embodiment according to the technique of the present disclosure is to provide an endoscope system, a medical information processing apparatus, a medical information processing method, a medical information processing program, and a recording medium capable of improving recognition accuracy of an audio input. The endoscope system according to an aspect of the present invention includes an audio input device; an image sensor that images a subject; and a processor, in which the processor acquires a plurality of medical images by causing the image sensor to image the subject in chronological order, accepts an input of an audio input trigger during capturing of the plurality of medical (Continued)

images, sets, in a case where the audio input trigger is input, an audio recognition dictionary according to the audio input trigger, and performs audio recognition on audio input to the audio input device after the setting, using the set audio recognition dictionary.

20 Claims, 19 Drawing Sheets

(51) Int. Cl.

| | |
|---|---|
| ***G06T 7/00*** | (2017.01) |
| ***G10L 15/08*** | (2006.01) |
| ***G10L 15/22*** | (2006.01) |

(52) U.S. Cl.

CPC .............. *G06V 10/70* (2022.01); *G10L 15/08* (2013.01); *G10L 15/22* (2013.01); *G06T 2207/10068* (2013.01); *G06T 2207/20081* (2013.01); *G06T 2207/30096* (2013.01); *G06V 2201/03* (2022.01); *G10L 2015/088* (2013.01)

(58) Field of Classification Search

CPC . G06T 2207/10068; G06T 2207/20081; G06T 2207/30096; G10L 15/08; G10L 15/22; G10L 2015/088

See application file for complete search history.

(56) References Cited

U.S. PATENT DOCUMENTS

| | | | | |
|---|---|---|---|---|
| 2017/0337683 | A1 * | 11/2017 | Yoshida | A61B 10/06 |
| 2019/0125319 | A1 * | 5/2019 | Enoki | A61B 34/25 |
| 2019/0180865 | A1 * | 6/2019 | Kashima | A61B 1/00186 |
| 2020/0242766 | A1 | 7/2020 | Endo | |
| 2021/0203875 | A1 * | 7/2021 | Sakurada | G11B 27/309 |
| 2022/0277449 | A1 | 9/2022 | Endo | |

FOREIGN PATENT DOCUMENTS

| | | | |
|---|---|---|---|
| JP | 2006136385 | | 6/2006 |
| JP | 2006136385 A | * | 6/2006 |
| JP | 2008136646 | | 6/2008 |
| JP | 2016158752 | | 9/2016 |
| JP | 2017221486 | | 12/2017 |
| JP | 2021037036 | | 3/2021 |
| WO | 2017187676 | | 11/2017 |
| WO | 2019078102 | | 4/2019 |

OTHER PUBLICATIONS

"International Search Report (Form PCT/ISA/210) of PCT/JP2022/033260", mailed on Nov. 8, 2022, with English translation thereof, pp. 1-7.

"Written Opinion of the International Searching Authority (Form PCT/ISA/237) of PCT/JP2022/033260", mailed on Nov. 8, 2022, with English translation thereof, pp. 1-10.

"Notice of reasons for refusal of Japan Counterpart Application", issued on Aug. 21, 2026, with English translation thereof, pp. 1-11.

* cited by examiner

ENDOSCOPE SYSTEM, MEDICAL INFORMATION PROCESSING APPARATUS, MEDICAL INFORMATION PROCESSING METHOD, MEDICAL INFORMATION PROCESSING PROGRAM, AND RECORDING MEDIUM

CROSS-REFERENCE TO RELATED APPLICATIONS

The present application is a Continuation of PCT International Application No. PCT/JP2022/033260 filed on Sep. 5, 2022 claiming priority under 35 U.S.C § 119(a) to Japanese Patent Application No. 2021-146308 filed on Sep. 8, 2021. Each of the above applications is hereby expressly incorporated by reference, in its entirety, into the present application.

BACKGROUND OF THE INVENTION

1. Field of the Invention

The present invention relates to an endoscope system, a medical information processing apparatus, a medical information processing method, a medical information processing program, and a recording medium which perform an audio input and audio recognition.

2. Description of the Related Art

In the technical field of performing an examination and diagnosis support using medical images, it is known to recognize an audio input by a user and to perform processing based on a recognition result. For example, JP1996-052105A (JP-H08-052105A) discloses that the endoscope is operated by the audio input. In addition, JP2004-102509A discloses that an audio input for report creation can be performed.

SUMMARY OF THE INVENTION

In a case of performing an audio input during an examination using medical images, in a case where all words can be recognized regardless of the scene, there is a risk that mutual erroneous recognition between words increases and operability is reduced. However, the techniques in the related art such as JP1996-052105A (JP-H08-052105A) and JP2004-102509A described above have not sufficiently taken these problems into consideration.

The present invention has been made in view of such circumstances, and an object thereof is to provide an endoscope system, a medical information processing apparatus, a medical information processing method, a medical information processing program, and a recording medium capable of improving the accuracy of the audio recognition regarding the medical images.

In order to achieve the object described above, an endoscope system according to a first aspect of the present invention is an endoscope system including an audio input device; an image sensor that images a subject; and a processor, in which the processor acquires a plurality of medical images obtained by the image sensor imaging the subject in chronological order, accepts an input of an audio input trigger during capturing of the plurality of medical images, sets, in a case where the audio input trigger is input, an audio recognition dictionary according to the audio input trigger, and performs audio recognition on audio input to the audio input device after the setting, using the set audio recognition dictionary. In the first aspect, since the audio recognition dictionary according to the audio input trigger is set and the audio recognition is performed using the set audio recognition dictionary, it is possible to improve the accuracy of the audio recognition regarding the medical image using the audio recognition dictionary tailored to a scene of the audio recognition.

In the endoscope system according to a second aspect, in the first aspect, in the audio recognition, the processor recognizes only registered words that are registered in the set audio recognition dictionary, and causes an output device to output a result of the audio recognition for the registered words. According to the second aspect, only the registered words registered in the set audio recognition dictionary are audio-recognized, so that recognition accuracy can be improved.

In the endoscope system according to a third aspect, in the first aspect, in the audio recognition, the processor recognizes registered words that are registered in the set audio recognition dictionary and specific words, and causes an output device to output a result of the audio recognition for the registered words among the recognized words. Note that an example of the "specific word" is a wake word for the audio input device, but the "specific word" is not limited thereto.

In the endoscope system according to a fourth aspect, in any one of the first to third aspects, the processor determines whether or not a specific subject is included in the plurality of medical images, using image recognition, and accepts a determination result indicating that the specific subject is included, as the audio input trigger.

In the endoscope system according to a fifth aspect, in any one of the first to fourth aspects, the processor determines whether or not a specific subject is included in the plurality of medical images, using image recognition, discriminates the specific subject in a case where it is determined that the specific subject is included, and accepts an output of a discrimination result for the specific subject, as the audio input trigger.

In the endoscope system according to a sixth aspect, in the fourth or fifth aspect, the processor determines whether or not a plurality of types of the specific subjects are included in the plurality of medical images, using a plurality of times of image recognition, respectively corresponding to the plurality of types of specific subjects, and sets the audio recognition dictionary corresponding to the type of the specific subject that is determined to be included in the plurality of medical images by any of the plurality of times of image recognition, among the plurality of types of specific subjects.

In the endoscope system according to a seventh aspect, in the sixth aspect, the processor determines whether or not a plurality of specific subjects are included in the plurality of medical images, using the image recognition, and sets the audio recognition dictionary corresponding to the specific subject determined to be included in the plurality of medical images, among the plurality of specific subjects.

In the endoscope system according to an eighth aspect, in any one of the fourth to seventh aspects, the processor performs the image recognition using an image recognizer configured by machine learning.

In the endoscope system according to a ninth aspect, in any one of the fourth to eighth aspects, the processor records the medical image decided to include the specific subject, among the plurality of medical images, a determination result using the image recognition for the specific subject, and a result of the audio recognition in a recording device in association with each other.

In the endoscope system according to a tenth aspect, in any one of the fourth to ninth aspects, the processor decides at least one of a lesion, a lesion candidate region, a landmark, a treated region, a treatment tool, or a hemostat, as the specific subject.

In the endoscope system according to an eleventh aspect, in any one of the fourth to tenth aspects, the processor executes the audio recognition using the set audio recognition dictionary during a period in which a predetermined condition is satisfied after the setting.

In the endoscope system according to a twelfth aspect, in the eleventh aspect, the processor sets the period for each image recognizer that performs the image recognition.

In the endoscope system according to a thirteenth aspect, in the eleventh or twelfth aspect, the processor sets the period depending on a type of the audio input trigger.

In the endoscope system according to a fourteenth aspect, in any one of the eleventh to thirteenth aspects, the processor displays a remaining time of the period on a screen of a display device.

In the endoscope system according to a fifteenth aspect, in any one of the first to fourteenth aspects, the processor performs the audio recognition for site information, findings information, treatment information, and hemostasis information.

In the endoscope system according to a sixteenth aspect, in any one of the first to fifteenth aspects, in a case where any one of an imaging start instruction of the plurality of medical images, an output of a result of image recognition for the plurality of medical images, an operation of switching to a discrimination mode, an operation to an operation device connected to the endoscope system, or an input of a wake word for the audio input device is performed, the processor decides that the audio input trigger is input.

In the endoscope system according to a seventeenth aspect, in any one of the first to sixteenth aspects, the processor displays a result of the audio recognition on a display device.

In order to achieve the object described above, a medical information processing apparatus according to an eighteenth aspect of the present invention is a medical information processing apparatus including a processor, in which the processor acquires a plurality of medical images obtained by an image sensor imaging a subject in chronological order, accepts an input of an audio input trigger during an input of the plurality of medical images, sets, in a case where the audio input trigger is input, an audio recognition dictionary according to the audio input trigger, and performs audio recognition on audio input to the audio input device after the setting, using the set audio recognition dictionary. According to the eighteenth aspect, it is possible to improve the accuracy of the audio recognition regarding the medical image as in the first aspect.

In order to achieve the object described above, a medical information processing method according to a nineteenth aspect of the present invention is a medical information processing method executed by an endoscope system including an audio input device, an image sensor that images a subject, and a processor, the medical information processing method including, via the processor, acquiring a plurality of medical images obtained by the image sensor imaging the subject in chronological order; accepting an input of an audio input trigger during capturing of the plurality of medical images; setting, in a case where the audio input trigger is input, an audio recognition dictionary according to the audio input trigger; and performing audio recognition on audio input to the audio input device after the setting, using the set audio recognition dictionary. According to the nineteenth aspect, it is possible to improve the recognition accuracy of the audio input regarding the medical image as in the first and eighteenth aspects. The nineteenth aspect may have the same configuration as the second to seventeenth aspects.

In order to achieve the object described above, a medical information processing program according to a twentieth aspect of the present invention is a medical information processing program causing an endoscope system including an audio input device, an image sensor that images a subject, and a processor, to execute a medical information processing method, the medical information processing program causing, in the medical information processing method, the processor to acquire a plurality of medical images obtained by the image sensor imaging the subject in chronological order, accept an input of an audio input trigger during capturing of the plurality of medical images, set, in a case where the audio input trigger is input, an audio recognition dictionary according to the audio input trigger, and perform audio recognition on audio input to the audio input device after the setting, using the set audio recognition dictionary. According to the twentieth aspect, it is possible to improve the accuracy of the audio recognition regarding the medical image as in the first, eighteenth, and nineteenth aspects.

The medical information processing method executed by the medical information processing program according to the twentieth aspect may have the same configuration as the second to seventeenth aspects.

In order to achieve the object described above, a recording medium according to a twenty-first aspect of the present invention is a non-transitory and tangible recording medium in which a computer readable code of the medical information processing program according to the twentieth aspect is recorded. In the twenty-first aspect, examples of the "non-transitory and tangible recording medium" include various magneto-optical recording devices and semiconductor memories. The "non-transitory and tangible recording medium" does not include a non-tangible recording medium such as a carrier wave signal itself and a propagation signal itself.

Note that, in the twenty-first aspect, the medical information processing program of which the code is recorded in the recording medium may be one that causes the endoscope system or the medical information processing apparatus to execute a medical information processing program that performs the same processing as in the second to seventeenth aspects.

With the endoscope system, the medical information processing apparatus, the medical information processing method, the medical information processing program, and the recording medium according to the present invention, it is possible to improve accuracy of audio recognition regarding medical images.

DESCRIPTION OF THE PREFERRED EMBODIMENTS

Embodiments of an endoscope system, a medical information processing apparatus, a medical information processing method, a medical information processing program, and a recording medium according to the present invention will be described. In the description, reference is made to the accompanying drawings as necessary. Note that, in the accompanying drawings, some constituents may be omitted for convenience of description.

First Embodiment

[Endoscopic Image Diagnosis Support System]

Here, a case where the present invention is applied to an endoscopic image diagnosis support system will be described as an example. The endoscopic image diagnosis support system is a system that supports detection and discrimination of a lesion or the like in an endoscopy. In the following, an example of application to an endoscopic image diagnosis support system that supports detection and discrimination of a lesion and the like in a lower digestive tract endoscopy (large intestine examination) will be described.

Figure 1:
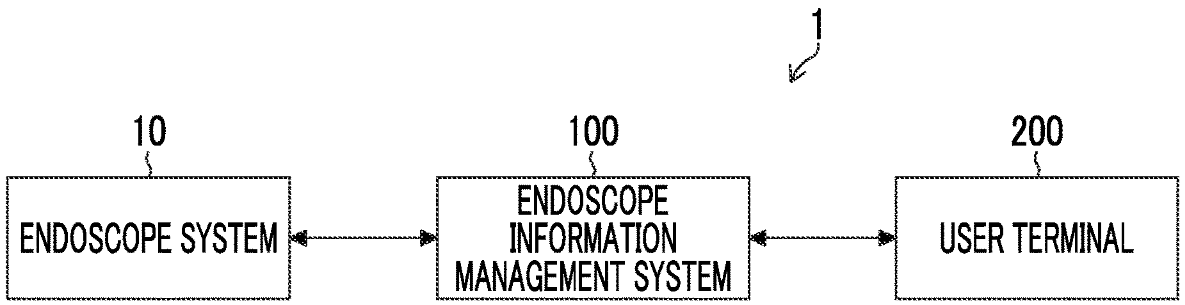
FIG. 1 is a diagram illustrating a schematic configuration of an endoscopic image diagnosis support system according to a first embodiment.

FIG. 1 is a block diagram illustrating an example of a schematic configuration of the endoscopic image diagnosis support system.

As illustrated in FIG. 1, an endoscopic image diagnosis support system 1 (endoscope system) of the present embodiment has an endoscope system 10 (endoscope system, medical information processing apparatus), an endoscope information management system 100, and a user terminal 200.

[Endoscope System]

Figure 2:
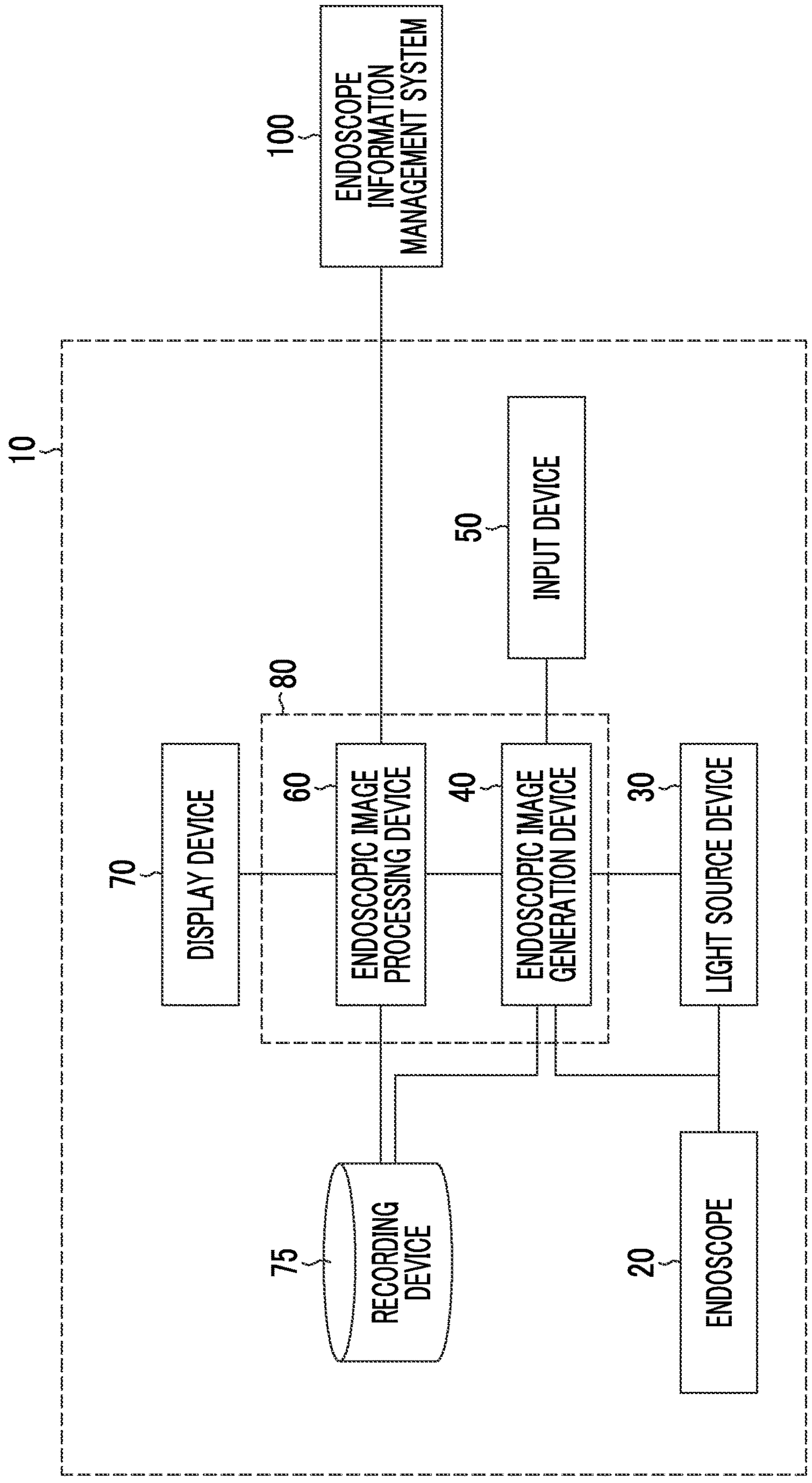
FIG. 2 is a diagram illustrating a schematic configuration of an endoscope system.

FIG. 2 is a block diagram illustrating a schematic configuration of the endoscope system 10.

The endoscope system 10 of the present embodiment is configured as a system capable of an observation using special light (special light observation) in addition to an observation using white light (white light observation). In the special light observation, a narrow-band light observation is included. In the narrow-band light observation, a blue laser imaging observation (BLI observation), a narrow band imaging observation (NBI observation; NBI is a registered trademark), a linked color imaging observation (LCI observation), and the like are included. Note that the special light observation itself is a well-known technique, so detailed description thereof will be omitted.

As illustrated in FIG. 2, the endoscope system 10 of the present embodiment has an endoscope 20, a light source device 30, an endoscopic image generation device 40, an endoscopic image processing device 60, a display device 70 (output device, display device), a recording device 75 (recording device), an input device 50, and the like. The endoscopic image generation device 40 and the endoscopic image processing device 60 constitute a medical information processing apparatus 80 (medical information processing apparatus)

[Endoscope]

Figure 3:
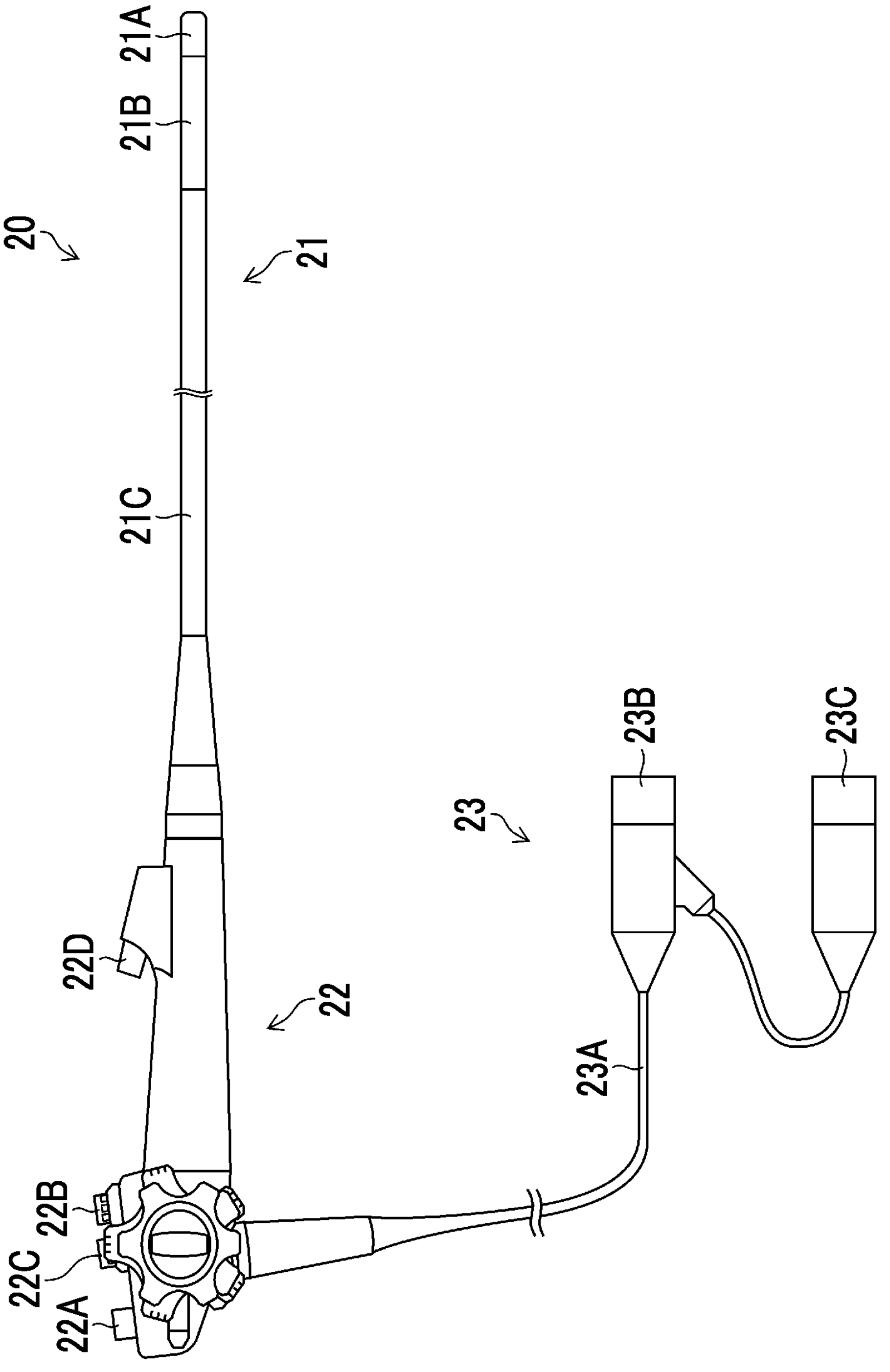
FIG. 3 is a diagram illustrating a schematic configuration of an endoscope.

FIG. 3 is a diagram illustrating a schematic configuration of the endoscope 20.

The endoscope 20 of the present embodiment is an endoscope for a lower digestive organ. As illustrated in FIG. 3, the endoscope 20 is a flexible endoscope (electronic endoscope), and has an insertion part 21, an operation part 22, and a connection part 23.

The insertion part 21 is a part to be inserted into a hollow organ (large intestine in the present embodiment). The insertion part 21 includes a distal end portion 21A, a bendable portion 21B, and a soft portion 21C in order from a distal end side.

Figure 4:
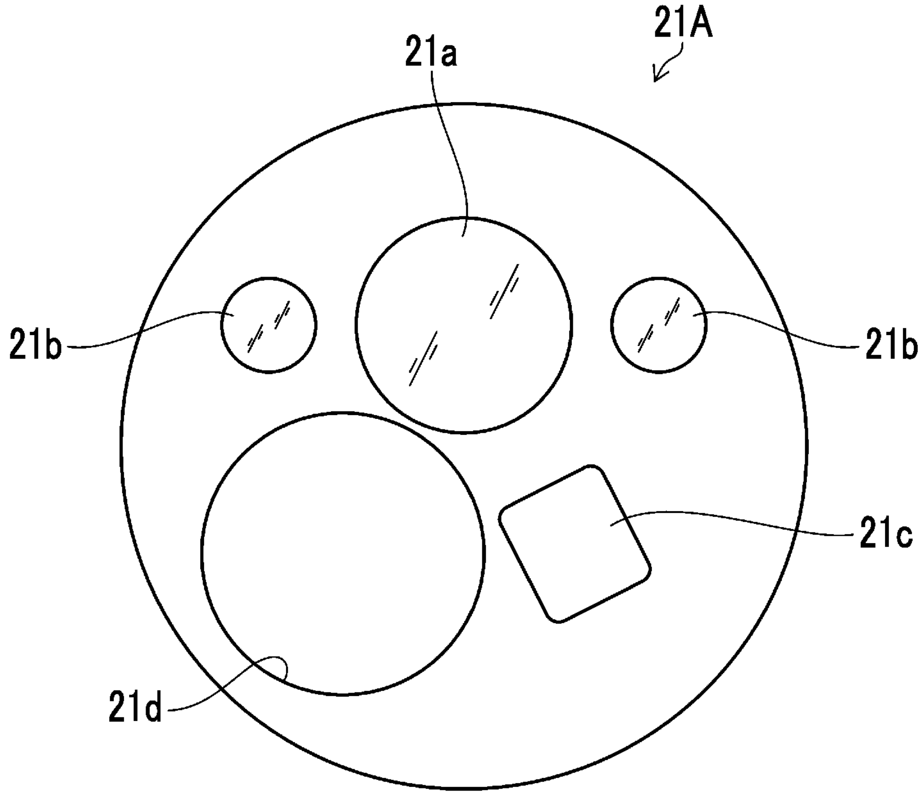
FIG. 4 is a diagram illustrating an example of a configuration of an edge surface of a distal end portion.

FIG. 4 is a diagram illustrating an example of a configuration of an edge surface of the distal end portion.

As illustrated in the figure, in the edge surface of the distal end portion 21A, an observation window 21*a*, illumination windows 21*b*, an air/water supply nozzle 21*c*, a forceps outlet 21*d*, and the like are provided. The observation window 21*a* is a window for an observation. The inside of the hollow organ is imaged through the observation window 21*a*. Imaging is performed via an optical system such as a lens and an image sensor (not illustrated) built in the distal end portion 21A (portion of the observation window 21*a*). As the image sensor, for example, a complementary metal-oxide-semiconductor image sensor (CMOS image sensor), a charge-coupled device image sensor (CCD image sensor), or the like is used. The illumination windows 21*b* are windows for illumination. The inside of the hollow organ is irradiated with illumination light via the illumination windows 21*b*. The air/water supply nozzle 21*c* is a nozzle for cleaning. A cleaning liquid and a drying gas are sprayed from the air/water supply nozzle 21*c* toward the observation window 21*a*. The forceps outlet 21*d* is an outlet for a treatment tool such as forceps. The forceps outlet 21*d* functions as a suction port for sucking body fluids and the like.

The bendable portion 21B is a portion that is bent according to an operation of an angle knob 22A of the operation part 22. The bendable portion 21B is bent in four directions of up, down, left, and right.

The soft portion 21C is an elongated portion provided between the bendable portion 21B and the operation part 22. The soft portion 21C has flexibility.

The operation part 22 is a part that is held by an operator to perform various operations. The operation part 22 includes various operation members. As an example, the operation part 22 includes the angle knob 22A for a bending operation of the bendable portion 21B, an air/water supply button 22B for performing an air/water supply operation, and a suction button 22C for performing a suction operation. In addition, the operation part 22 includes an operation member (shutter button) for imaging a static image, an operation member for switching an observation mode, an operation member for switching on and off of various support functions, and the like. In addition, the operation part 22 includes a forceps insertion port 22D for inserting a treatment tool such as forceps. The treatment tool inserted from the forceps insertion port 22D is drawn out from the forceps outlet 21*d* (refer to FIG. 4) on a distal end of the insertion part 21. As an example, the treatment tool includes biopsy forceps, snares, and the like.

The connection part 23 is a part for connecting the endoscope 20 to the light source device 30, the endoscopic image generation device 40, and the like. The connection part 23 includes a cord 23A extending from the operation part 22, and a light guide connector 23B and a video connector 23C that are provided on a distal end of the cord 23A. The light guide connector 23B is a connector for connecting to the light source device 30. The video connector 23C is a connector for connecting to the endoscopic image generation device 40.

[Light Source Device]

The light source device 30 generates illumination light. As described above, the endoscope system 10 of the present embodiment is configured as a system capable of the special light observation in addition to the normal white light observation. Therefore, the light source device 30 is configured to be capable of generating light (for example, narrow-band light) corresponding to the special light observation in addition to the normal white light. Note that, as described above, the special light observation itself is a well-known technique, so the description for the light generation will be omitted.

Medical Information Processing Apparatus

[Endoscopic Image Generation Device]

The endoscopic image generation device 40 (processor) comprehensively controls the entire operation of the endoscope system 10 together with the endoscopic image processing device 60 (processor). The endoscopic image generation device 40 includes, as a hardware configuration, a processor, a main storage unit (memory), an auxiliary storage unit (memory), a communication unit, and the like. That is, the endoscopic image generation device 40 has a so-called computer configuration as the hardware configuration. The processor is configured by, for example, a central processing unit (CPU), a graphics processing unit (GPU), a field-programmable gate array (FPGA), a programmable logic device (PLD), and the like. For example, the main storage unit is configured by a random-access memory (RAM) and the like. The auxiliary storage unit is configured by, for example, a non-transitory and tangible recording medium such as a flash memory, and can record computer-readable codes of a medical information processing program according to the embodiment of the present invention or of a part thereof, and other data. In addition, the auxiliary storage unit may include various magneto-optical recording devices, semiconductor memories, and the like in addition to or instead of the flash memory.

Figure 5:
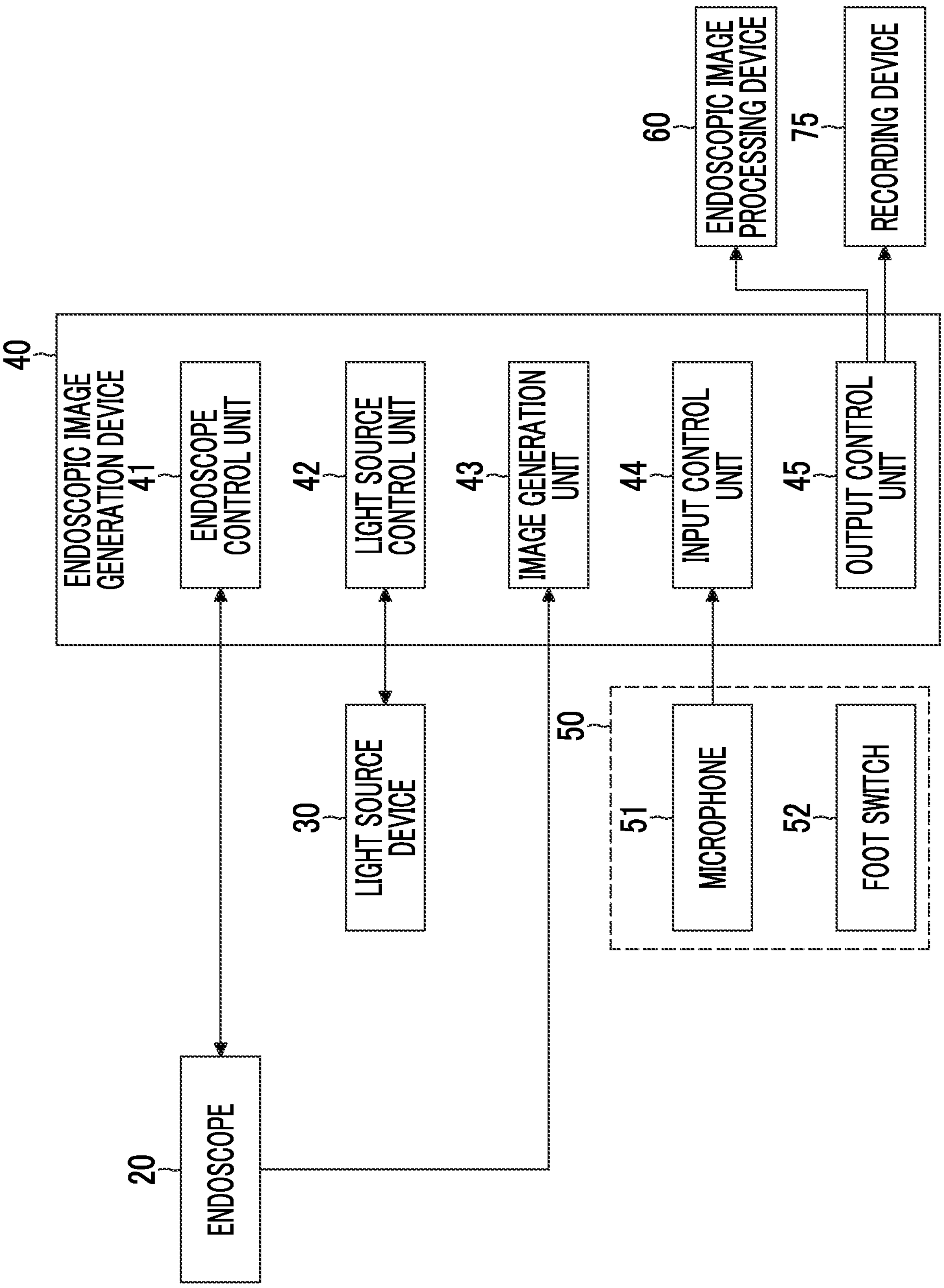
FIG. 5 is a block diagram illustrating main functions of an endoscopic image generation device.

FIG. 5 is a block diagram illustrating main functions of the endoscopic image generation device 40.

As illustrated in the figure, the endoscopic image generation device 40 has functions of an endoscope control unit 41, a light source control unit 42, an image generation unit 43, an input control unit 44, an output control unit 45, and the like. Various programs executed by the processor (which may include the medical information processing program according to the embodiment of the present invention or a part thereof) and various kinds of data necessary for control or the like are stored in the auxiliary storage unit described above, and each function of the endoscopic image generation device 40 is realized by the processor executing these programs. The processor of the endoscopic image generation device 40 is an example of the processor in the endoscope system and in the medical information processing apparatus according to the embodiment of the present invention.

The endoscope control unit 41 controls the endoscope 20. The control for the endoscope 20 includes image sensor drive control, air/water supply control, suction control, and the like.

The light source control unit 42 controls the light source device 30. The control for the light source device 30 includes light emission control for a light source, and the like.

The image generation unit 43 generates captured images (endoscopic images) on the basis of signals output from the image sensor of the endoscope 20. The image generation unit 43 can generate a static image and/or a video (a plurality of medical images obtained by an image sensor 25 imaging a subject in chronological order) as the captured image. The image generation unit 43 may perform various kinds of image processing on the generated images.

The input control unit 44 accepts an input of an operation and an input of various kinds of information via the input device 50.

The output control unit 45 controls an output of information to the endoscopic image processing device 60. The information to be output to the endoscopic image processing device 60 includes various kinds of operation information input from the input device 50, and the like in addition to the endoscopic image obtained by imaging.

[Input Device]

The input device 50 constitutes a user interface in the endoscope system 10 together with the display device 70. The input device 50 includes a microphone 51 (audio input device) and a foot switch 52 (operation device). The microphone 51 is an input device for performing audio recognition, which will be described later. The foot switch 52 is an operation device that is placed at an operator's feet and operated with the foot, and outputs an operation signal (for example, a signal indicating an audio input trigger or a signal to select a candidate for audio recognition) by stepping on a pedal. Note that, in this embodiment, the microphone 51 and the foot switch 52 are controlled by the input control unit 44 of the endoscopic image generation device 40, but the present invention is not limited to this embodiment, and the microphone 51 and the foot switch 52 may also be controlled via the endoscopic image processing device 60, the display device 70, and the like. In addition, in the operation part 22 of the endoscope 20, an operation device (button, switch, and the like) having the same function as the foot switch 52 may be provided.

In addition, the input device 50 can include a known input device such as a keyboard, a mouse, a touch panel, and a gaze input device as the operation device.

[Endoscopic Image Processing Device]

The endoscopic image processing device 60 includes, as a hardware configuration, a processor, a main storage unit, an auxiliary storage unit, a communication unit, and the like. That is, the endoscopic image processing device 60 has a so-called computer configuration as the hardware configuration. The processor is configured by, for example, a CPU, a graphics processing unit (GPU), a field-programmable gate array (FPGA), a programmable logic device (PLD), and the like. The processor of the endoscopic image processing device 60 is an example of the processor in the endoscope system and in the medical information processing apparatus according to the embodiment of the present invention. The processor of the endoscopic image generation device 40 and the processor of the endoscopic image processing device 60 may share the functions of the processor in the endoscope system and in the medical information processing apparatus according to the embodiment of the present invention. For example, a form can be adopted in which the endoscopic image generation device 40 mainly has a function of an "endoscope processor" that generates endoscopic images, and in which the endoscopic image processing device 60 mainly has a function of a "computer-aided diagnosis (CAD) box" that performs image processing on the endoscopic images. However, in the present invention, a form different from such sharing of functions may be adopted.

For example, the main storage unit is configured by a memory such as a RAM. The auxiliary storage unit is configured by, for example, a non-transitory and tangible recording medium (memory) such as a flash memory, and stores computer-readable codes of various programs (which may include the medical information processing program according to the embodiment of the present invention or a part thereof) executed by the processor, and various kinds of data necessary for control or the like. In addition, the auxiliary storage unit may include various magneto-optical recording devices, semiconductor memories, and the like in addition to or instead of the flash memory. For example, the communication unit is configured by a communication interface connectable to a network. The endoscopic image processing device 60 is communicably connected to the endoscope information management system 100 via the communication unit.

Figure 6:
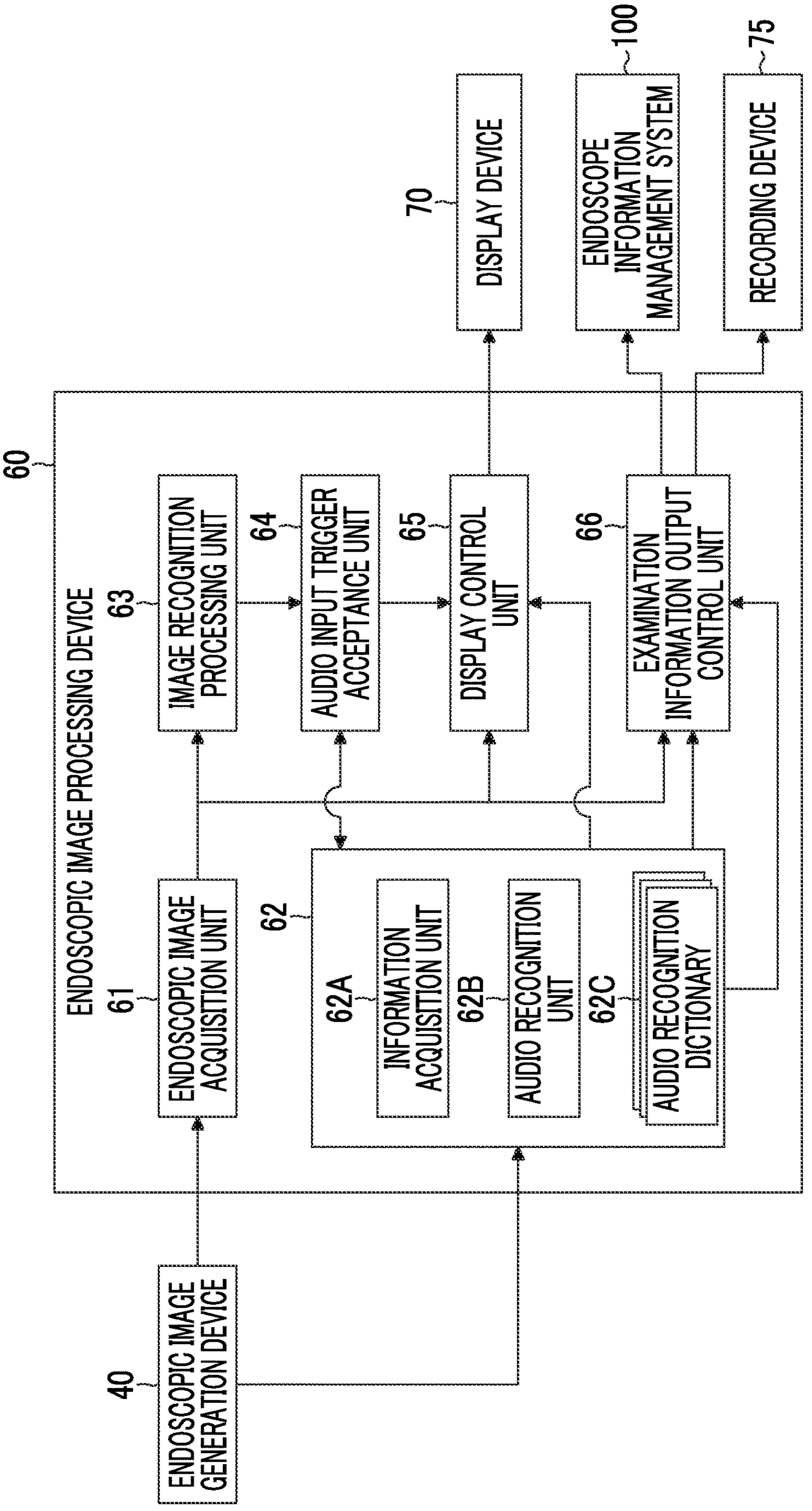
FIG. 6 is a block diagram illustrating main functions of an endoscopic image processing device.

FIG. 6 is a block diagram illustrating main functions of the endoscopic image processing device 60.

As illustrated in the figure, the endoscopic image processing device 60 mainly has functions of an endoscopic image acquisition unit 61, an input information acquisition unit 62, an image recognition processing unit 63, an audio input trigger acceptance unit 64, a display control unit 65, an examination information output control unit 66, and the like. These functions are realized by the processor executing the program (which may include the medical information processing program according to the embodiment of the present invention or a part thereof) stored in the auxiliary storage unit or the like.

[Endoscopic Image Acquisition Unit]

The endoscopic image acquisition unit 61 acquires an endoscopic image from the endoscopic image generation device 40. Acquisition of images can be performed in real time. That is, a plurality of medical images obtained by the image sensor 25 (image sensor) imaging the subject in chronological order can be sequentially acquired (sequentially input) in real time.

[Input Information Acquisition Unit]

The input information acquisition unit 62 (processor) acquires information input via the input device 50 and the endoscope 20. The input information acquisition unit 62 includes an information acquisition unit 62A that mainly acquires input information other than the audio information, an audio recognition unit 62B that acquires the audio information and that recognizes audio input via the microphone 51, and an audio recognition dictionary 62C used for audio recognition. The audio recognition dictionary 62C may include a plurality of dictionaries with different contents (for example, dictionaries regarding site information, findings information, treatment information, and hemostasis information).

Information input to the input information acquisition unit 62 via the input device 50 includes information (for example, audio information, an audio input trigger, and information on a candidate selection operation) input via the microphone 51, the foot switch 52, or a keyboard or mouse (not illustrated). In addition, the information input via the endoscope 20 includes information on an imaging start instruction for an endoscopic image (video), an imaging instruction for a static image, and the like. As described later, in the present embodiment, a user can input the audio input trigger, perform the selection operation of the audio recognition candidate, and the like via the microphone 51 and/or the foot switch 52. The input information acquisition unit 62 acquires operation information of the foot switch 52 via the endoscopic image generation device 40.

[Image Recognition Processing Unit]

The image recognition processing unit 63 (processor) performs image recognition on the endoscopic image acquired by the endoscopic image acquisition unit 61. The image recognition processing unit 63 can perform image recognition in real time.

Figure 7:
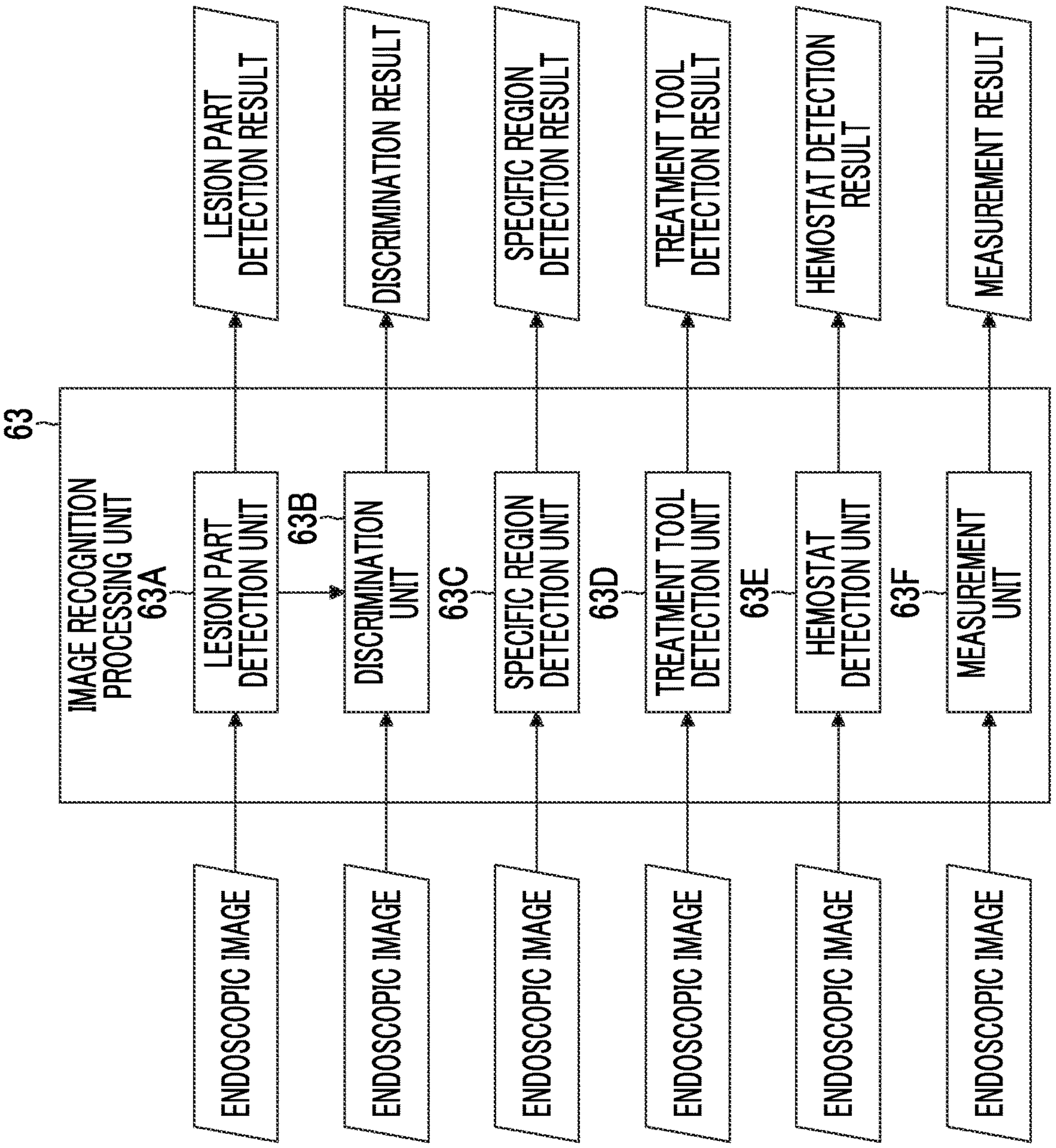
FIG. 7 is a block diagram illustrating main functions of an image recognition processing unit.

FIG. 7 is a block diagram illustrating main functions of the image recognition processing unit 63. As illustrated in the figure, the image recognition processing unit 63 has functions of a lesion part detection unit 63A, a discrimination unit 63B, a specific region detection unit 63C, a treatment tool detection unit 63D, a hemostat detection unit 63E, a measurement unit 63F, and the like. Each of these units can be used to determine or decide "whether or not a specific subject is included in an endoscopic image". The "specific subject" may be different depending on each unit of the image recognition processing unit 63, as described below.

The lesion part detection unit 63A detects a lesion part (lesion; an example of a "specific subject") such as a polyp from the endoscopic image. The processing of detecting the lesion part includes processing of detecting a part with a possibility of a lesion (benign tumor, dysplasia, or the like; lesion candidate region), processing of recognizing a region after the lesion is treated (treated region) and a part with features that may be directly or indirectly associated with a lesion (erythema or the like), and the like in addition to processing of detecting a part that is definitely a lesion part.

In a case where the lesion part detection unit 63A determines that "the lesion part (specific subject) is included in the endoscopic image", the discrimination unit 63B performs discrimination processing on the lesion part detected by the lesion part detection unit 63A. In the present embodiment, the discrimination unit 63B performs neoplastic or non-neoplastic (hyperplastic) discrimination processing on the lesion part such as a polyp detected by the lesion part detection unit 63A. Note that the discrimination unit 63B can be configured to output a discrimination result in a case where predetermined criteria are satisfied. As the "predetermined criteria", for example, a "case where a reliability degree (depending on conditions such as exposure, degree of focus, and blurring of an endoscopic image) of the discrimination result or a statistical value thereof (maximum, minimum, average, or the like within a predetermined period) is equal to or greater than a threshold value" can be adopted, but other criteria may be used.

The specific region detection unit 63C performs processing of detecting a specific region (landmark) in the hollow organ from the endoscopic image. For example, processing of detecting an ileocecum of the large intestine or the like is performed. The large intestine is an example of a hollow organ, and the ileocecum is an example of a specific region. For example, the specific region detection unit 63C may detect a hepatic flexure (right colon), a splenic flexure (left colon), a rectosigmoid, and the like. In addition, the specific region detection unit 63C may detect a plurality of specific regions.

The treatment tool detection unit 63D performs processing of detecting a treatment tool appearing in the image from the endoscopic image, and discriminating the type of the treatment tool. The treatment tool detection unit 63D can be configured to detect a plurality of types of treatment tools such as biopsy forceps and snares. Similarly, the hemostat detection unit 63E performs processing of detecting a hemostat such as a hemostatic clip and discriminating a type of the hemostat. The treatment tool detection unit 63D and the hemostat detection unit 63E may be configured by one image recognizer.

The measurement unit 63F performs measurements (measurements of shape, dimension, and the like) of a lesion, a lesion candidate region, a specific region, a treated region, and the like.

Each unit (the lesion part detection unit 63A, the discrimination unit 63B, the specific region detection unit 63C, the treatment tool detection unit 63D, the hemostat detection unit 63E, the measurement unit 63F, and the like) of the image recognition processing unit 63 can be configured using image recognizers (trained models) configured by machine learning. Specifically, each unit described above can be configured by image recognizers (trained models) trained using a machine learning algorithm such as a neural network (NN), a convolutional neural network (CNN), AdaBoost, and random forest. In addition, as described above regarding the discrimination unit 63B, each of these units can perform an output based on the reliability degree of a final output (discrimination results, type of treatment tool, and the like) by setting a network layer configuration as necessary. In addition, each unit described above may perform image recognition for all frames of the endoscopic image, or may perform image recognition for some frames intermittently.

As described below, the output of the recognition result of the endoscopic image from each of these units or the output of the recognition result satisfying the predetermined criteria (threshold value or the like of the reliability degree) may be used as the audio input trigger, and a period in which such an output is performed may be used as a period in which audio recognition is executed.

In addition, instead of configuring some or all of respective units constituting the image recognition processing unit 63 using the image recognizer (trained model), it is possible to adopt a configuration of calculating a feature amount from the endoscopic image and performing detection or the like using the calculated feature amount.

[Audio Input Trigger Acceptance Unit]

The audio input trigger acceptance unit 64 (processor) accepts an input of an audio input trigger while capturing (inputting) an endoscopic image, and sets the audio recognition dictionary 62C according to the input audio input trigger. The audio input trigger in the present embodiment is, for example, a determination result (detection result) indicating that a specific subject is included in the endoscopic image, and in this case, an output of the lesion part detection unit 63A can be used as the determination result. In addition, another example of the audio input trigger is an output of a discrimination result for the specific subject, and in this case, an output of the discrimination unit 63B can be used as the discrimination result. As still other examples of the audio input trigger, an imaging start instruction of a plurality of medical images, an input of a wake word for the microphone 51 (audio input device), an operation of the foot switch 52, an operation for another operation device (for example, colonofiberscope position determination device) connected to the endoscope system, and the like can be used. The settings of the audio recognition dictionary and the audio recognition according to these audio input triggers will be described in detail later.

[Display Control Unit]

The display control unit 65 (processor) controls display of the display device 70. In the following, main display control performed by the display control unit 65 will be described.

Figure 8:
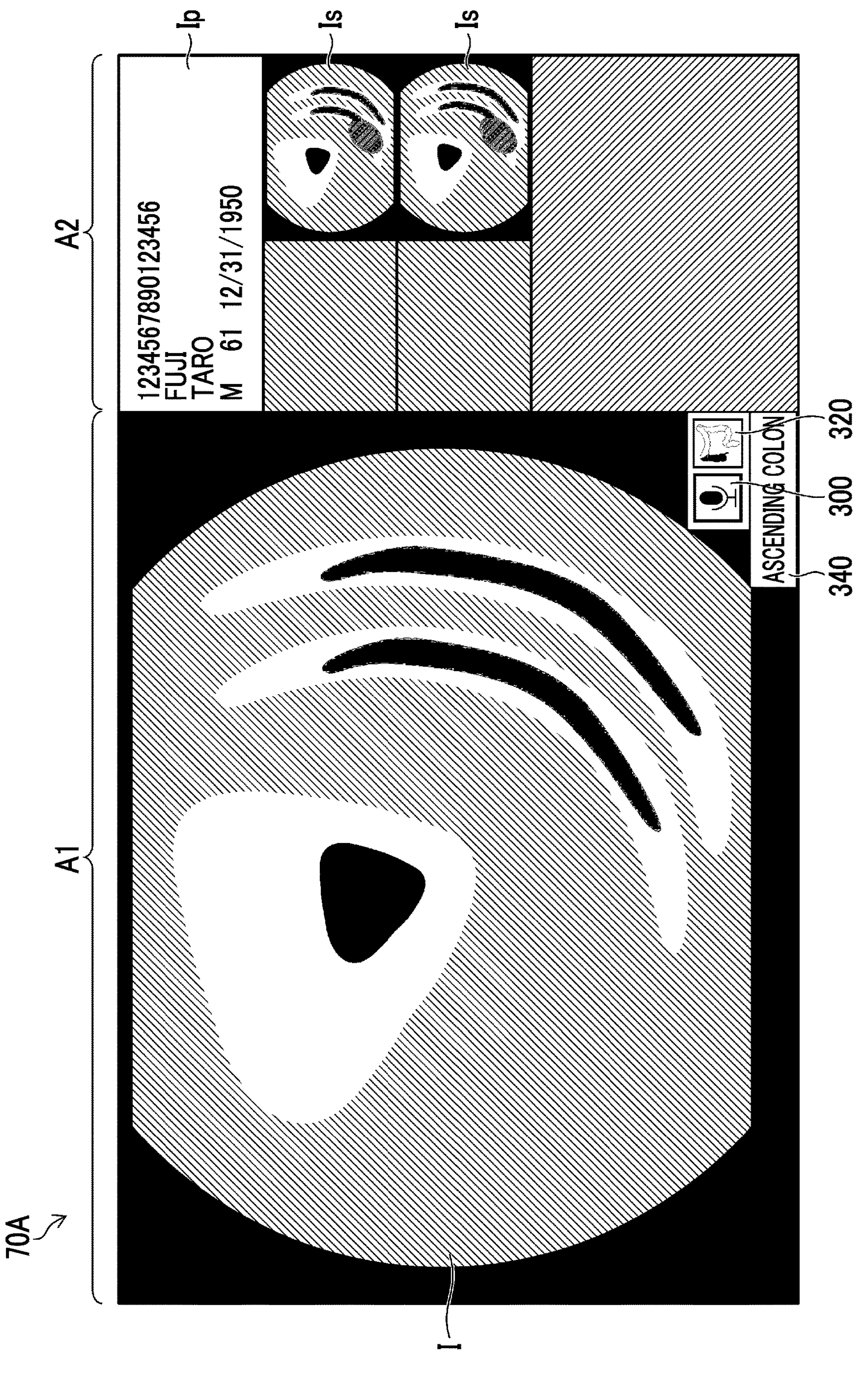
FIG. 8 is a diagram illustrating an example of a screen display during an examination.

The display control unit 65 displays the image (endoscopic image) captured by the endoscope 20 on the display device 70 in real time during the examination (imaging). FIG. 8 is a diagram illustrating an example of a screen display during the examination. As illustrated in the figure, an endoscopic image I (live view) is displayed in a main display region A1 set on a screen 70A. A secondary display region A2 is further set on the screen 70A, and various kinds of information regarding the examination are displayed. In the example illustrated in FIG. 8, a case where information Ip regarding a patient and a static image Is of the endoscopic image captured during the examination are displayed in the secondary display region A2 is illustrated. For example, the static images Is are displayed in the captured order from top to bottom of the screen 70A.

In addition, the display control unit 65 can display, on the screen 70A, an icon 300 indicating a state of the audio recognition, an icon 320 indicating a site being imaged, and a display region 340 where a site of an imaging target (ascending colon, transverse colon, descending colon, or the like) and a result of the audio recognition are displayed in text in real time (without time delay). The display control unit 65 can acquire information on a site via image recognition from the endoscopic image, a user's input via the operation device, an external device (for example, endoscope position detecting unit) connected to the endoscope system 10, or the like.

In addition, as described below, the display control unit 65 can display (output) a result of the audio recognition on the display device 70 (output device, display device).

[Examination Information Output Control Unit]

The examination information output control unit 66 outputs examination information to the recording device 75 and/or the endoscope information management system 100. For example, the examination information includes an endoscopic image captured during an examination, a determination result for a specific subject, a result of audio recognition, information on a site input during an examination, information on a treatment name input during an examination, information on a treatment tool detected during an examination, and the like. For example, the examination information is output for each lesion or each time a specimen is collected. In this case, respective pieces of information are output in association with each other. For example, the endoscopic image in which the lesion part or the like is imaged is output in association with the information on the site being selected. In addition, in a case where a treatment is performed, the information on the selected treatment name and the information on the detected treatment tool are output in association with the endoscopic image and the information on the site. In addition, the endoscopic image captured separately from the lesion part or the like is always output to the recording device 75 and/or the endoscope information management system 100. The endoscopic image is output with the information of imaging date and time added.

[Recording Device]

The recording device 75 (recording device) includes various magneto-optical recording devices or semiconductor memories, and control devices thereof, and can record endoscopic images (videos, static images), results of image recognition, results of audio recognition, examination information, report creation support information, and the like. These pieces of information may be recorded in a secondary storage unit of the endoscopic image generation device 40 or of the endoscopic image processing device 60, or in a recording device of the endoscope information management system 100.

[Audio Recognition in Endoscope System]

Audio recognition in the endoscope system 10 configured as described above will be described below.

[Outline of Audio Recognition]

Figure 9:
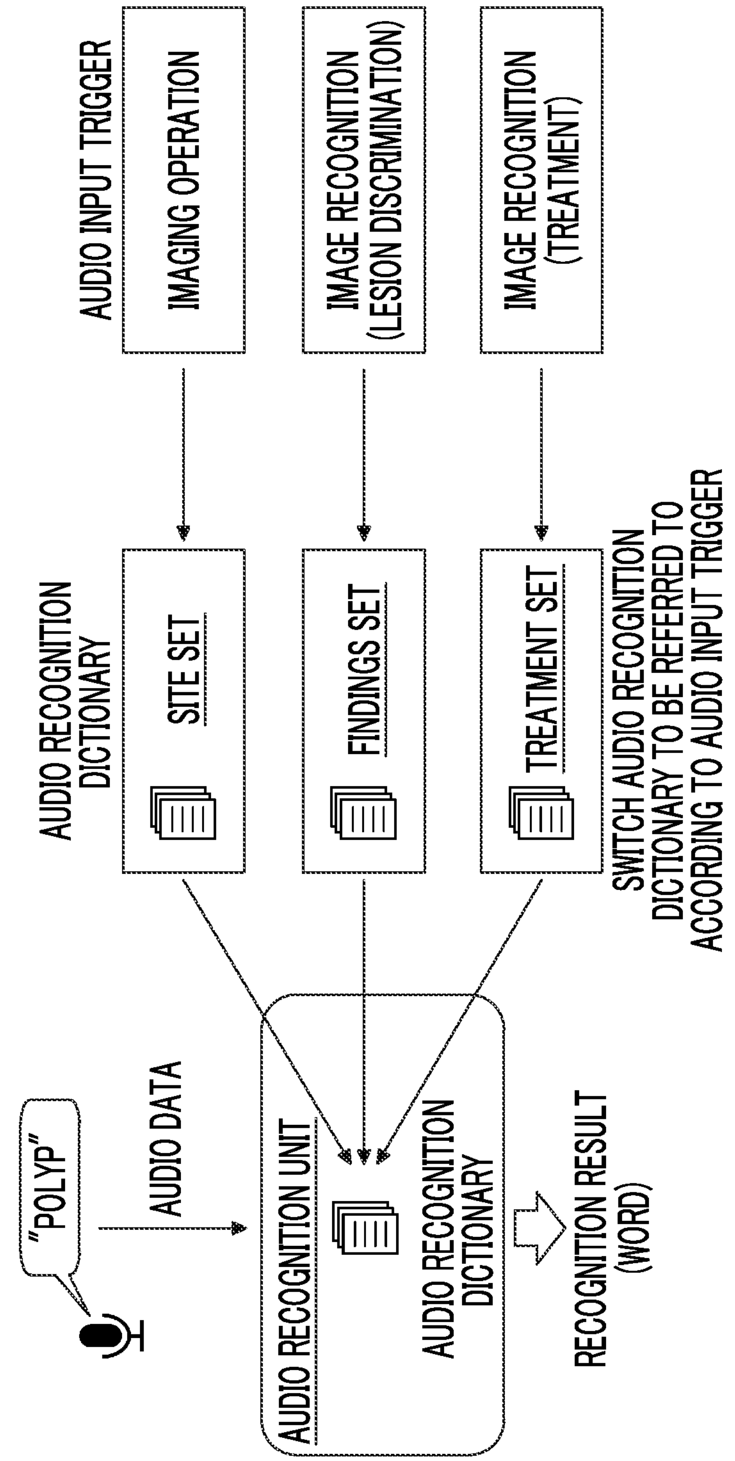
FIG. 9 is a diagram illustrating an outline of audio recognition.
Figure 10A:
FIGS. 10A to 10E are diagrams illustrating settings of an audio recognition dictionary.
Figure 10B:
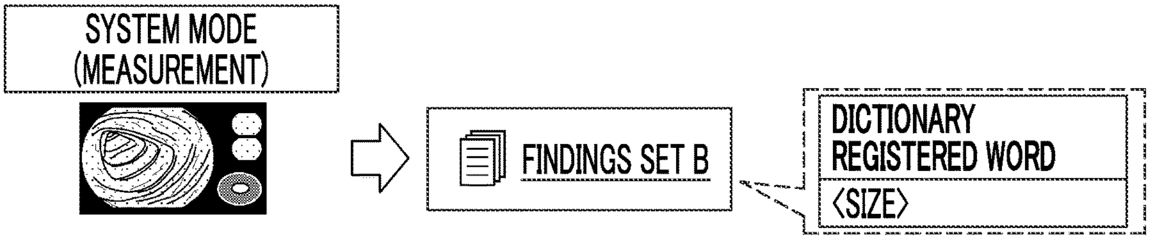
Figure 10C:
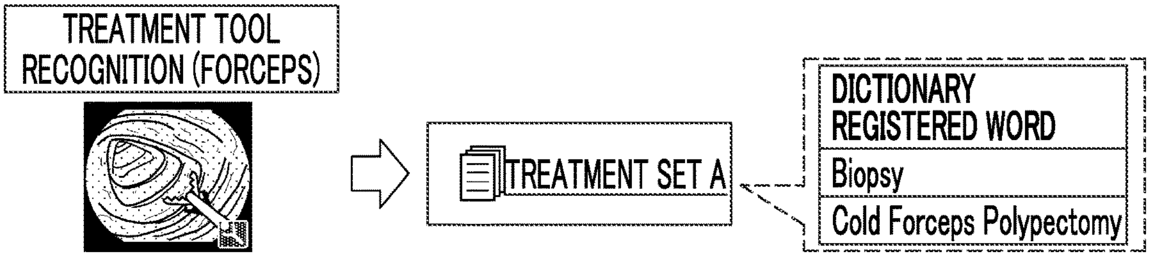
Figure 10D:
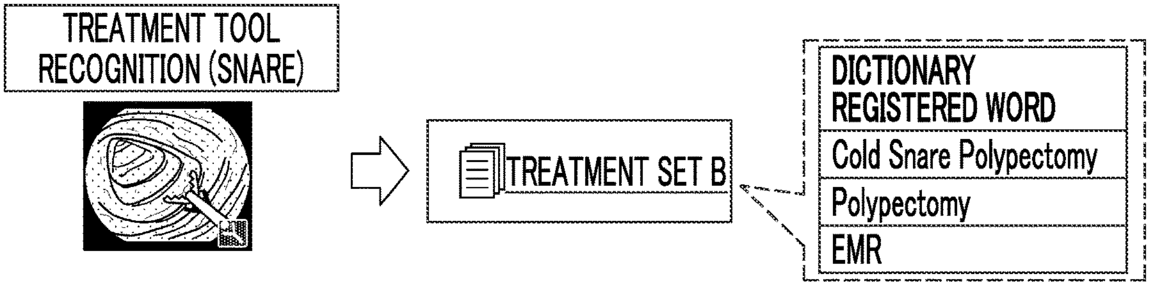
Figure 10E:
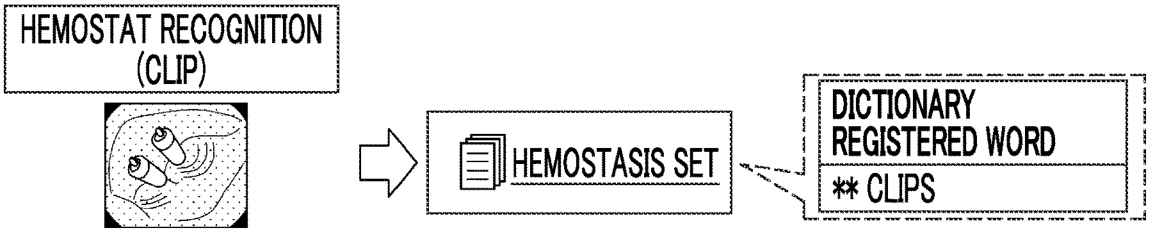

FIG. 9 is a diagram illustrating an outline of audio recognition. As illustrated in the figure, the medical information processing apparatus 80 (processor) accepts an input of an audio input trigger while capturing the endoscopic image (sequentially inputting), sets an audio recognition dictionary according to the audio input trigger in a case where the audio input trigger is input, and performs audio recognition on the audio input via the microphone 51 (audio input device) after the audio recognition dictionary is set, using the set audio recognition dictionary. As described above, the medical information processing apparatus 80 decides that an output of the detection result from the lesion part detection unit 63A, an output of the discrimination result from the discrimination unit 63B, an imaging start instruction of a plurality of medical images, a switching operation from a detection mode to a discrimination mode, an input of a wake word for the microphone 51 (audio input device), an operation of the foot switch 52, an input of an operation for an operation device connected to the endoscope system, or the like is an "input of the audio input trigger", and performs audio recognition.

Note that the start of the audio recognition may be delayed for the settings of the audio recognition dictionary, but it is preferable that the audio recognition is started (zero delay time) immediately after the audio recognition dictionary is set.

[Settings of Audio Recognition Dictionary]

FIGS. 10A to 10E are diagrams illustrating settings of the audio recognition dictionary. In each of FIGS. 10A to 10E, a left side of an arrow indicates the audio input trigger, and a right side of an arrow indicates an example of the audio recognition dictionary set according to the audio input trigger and registered words. As illustrated in FIGS. 10A to 10E, in a case where the audio input trigger is input, the audio recognition unit 62B sets the audio recognition dictionary 62C according to the audio input trigger. For example, in a case where the discrimination unit 63B outputs a discrimination result, the audio recognition unit 62B sets a "findings set A" as the audio recognition dictionary.

Figure 11A:
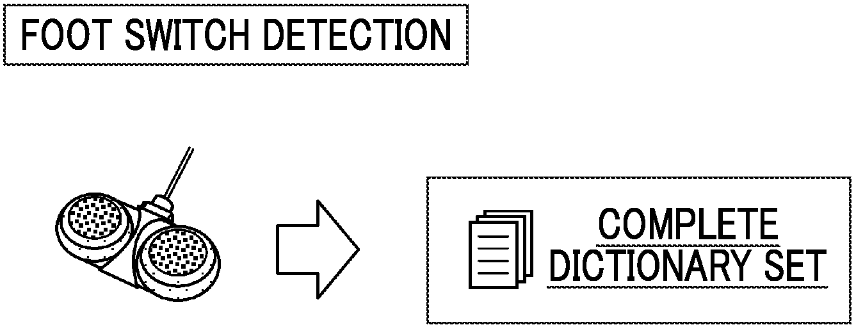
FIGS. 11A and 11B are other diagrams illustrating settings of the audio recognition dictionary.
Figure 11B:
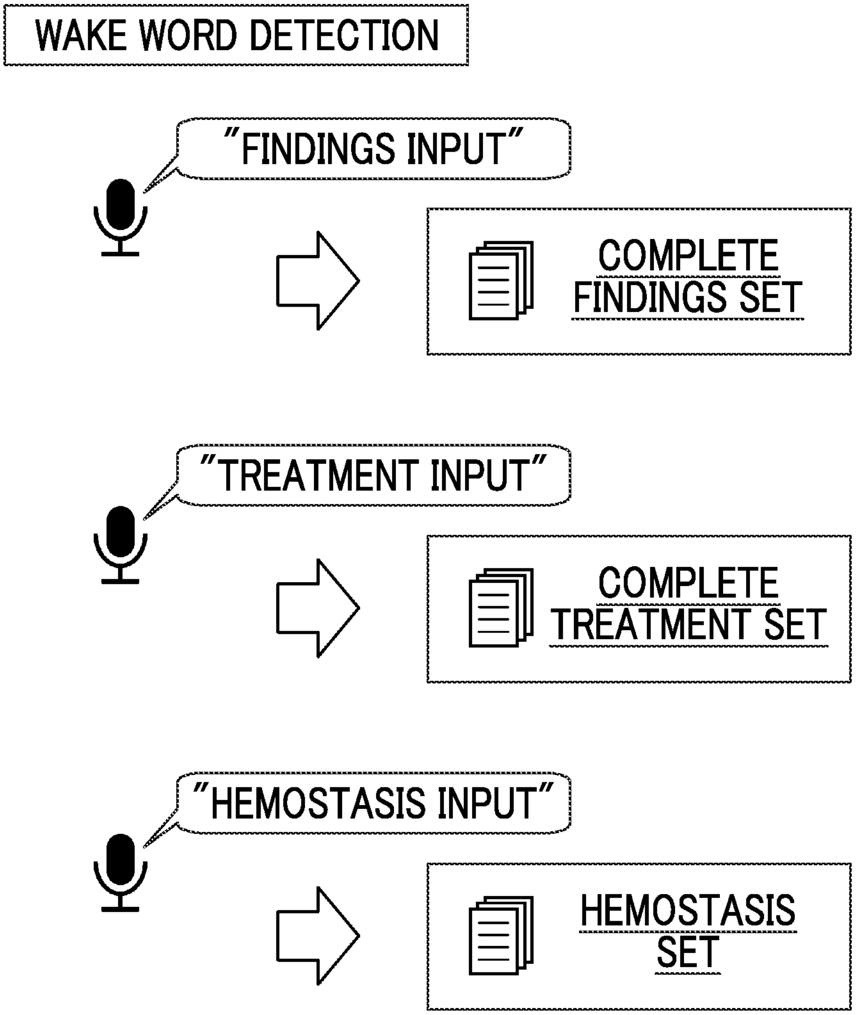

FIGS. 11A and 11B are other diagrams illustrating settings of the audio recognition dictionary. As illustrated in FIGS. 11A and 11B, the audio recognition unit 62B sets a "complete dictionary set" in a case of accepting an operation of the foot switch 52 (operation device) as the audio input trigger, and sets the audio recognition dictionary according to the contents of a wake word in a case of accepting an input of the wake word for the microphone 51 (audio input device) as the audio input trigger. Note that a "wake word" or a "wakeup word" can be defined as, for example, "a predetermined phrase for causing the audio recognition unit 62B to set the audio recognition dictionary and to start the audio recognition".

The wake words (wakeup words) described above can be divided into two types. The two types are a "wake word regarding a report input" and a "wake word regarding imaging mode control". The "wake word regarding a report input" is, for example, a "findings input" and a "treatment input". After such a wake word is recognized, the audio recognition dictionary for "findings" and "treatment" is set, and in a case where a word in the dictionary is recognized, the result of the audio recognition is output. The result of the audio recognition can be associated with the image or used in a report. The association with the image and the use in the report are a form of an "output" of the result of the audio recognition, and the display device 70, the recording device 75, the storage unit of the medical information processing apparatus 80, or the recording device of the endoscope information management system 100 or the like is a form of an "output device".

The other "wake word regarding imaging mode control" is, for example, "imaging setting" and "setting". After such a wake word is recognized, it is possible to set a dictionary used to turn on/off or switch a light source with audio (for example, by audio recognition of words such as "white", "LCI", and "BLI"), or to turn on/off (for example, by audio recognition of words such as "detection on" and "detection off") the lesion detection using an endoscope AI (recognizer using artificial intelligence). Note that the "output" and the "output device" are the same as described above for the "wake word regarding a report input".

[Time Chart of Audio Recognition Dictionary Settings]

Figure 12:
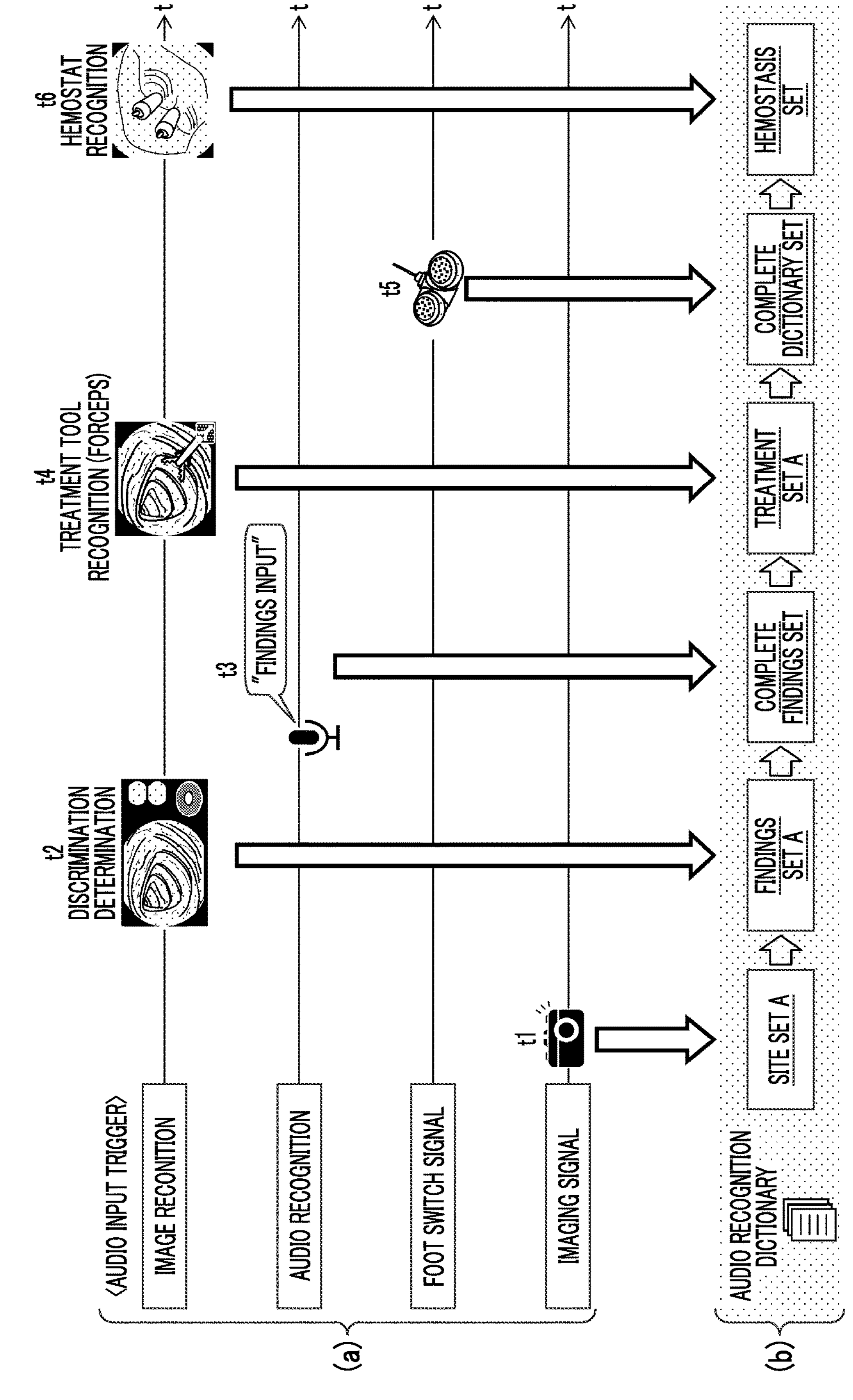
FIG. 12 is a time chart of setting the audio recognition dictionary.

FIG. 12 is a time chart of setting the audio recognition dictionary. Note that, in FIG. 12, specific phrases that are input by audio and the recognition results thereof are not illustrated. The (a) part of FIG. 12 illustrates the types of audio input triggers. In the example illustrated in the (a) part of FIG. 12, the audio input triggers are an output of a result of image recognition of the endoscopic image, an input of a wake word for the microphone 51, a signal from an operation of the foot switch 52 (operation device), and an imaging start instruction of the endoscopic image. In addition, the (b) part of FIG. 12 illustrates the audio recognition dictionaries set according to the audio input triggers. The audio recognition unit 62B sets different audio recognition dictionaries according to the flow of the examination (start of imaging, discovery of a lesion or a lesion candidate, a findings input, insertion of a treatment tool and treatment, and hemostasis).

In the endoscope system 10, image recognition (as a whole, a plurality of times of image recognition) corresponding to a plurality of types of "specific subjects" (specifically, the lesion, the treatment tool, the hemostat, and the like described above) as the determination (recognition) target can be performed by each unit of the image recognition processing unit 63, and the audio recognition unit 62B can set the audio recognition dictionary corresponding to the type of the "specific subject" determined to be "included in the endoscopic image" by any image recognition by each unit.

In addition, in the endoscope system 10, whether or not a plurality of "specific subjects" are included in the endoscopic image is determined by each unit, and the audio recognition unit 62B can set the audio recognition dictionary corresponding to the specific subject determined to be "included in the endoscopic image" among the plurality of "specific subjects". As a case where a plurality of "specific subjects" are included in the endoscopic image, for example, a case where a plurality of lesion parts are included, a case where a plurality of treatment tools are included, a case where a plurality of hemostats are included, and the like are considered.

Note that, for some image recognition among a plurality of times of image recognition by the respective units, the audio recognition dictionary may be set according to the type of the "specific subject".

[Audio Recognition]

The audio recognition unit 62B performs audio recognition on the audio input to the microphone 51 (audio input device) after the audio recognition dictionary is set, using the set audio recognition dictionary (illustration is omitted in FIG. 12). It is preferable that the display control unit 65 displays the result of the audio recognition on the display device 70.

In the present embodiment, the audio recognition unit 62B can perform audio recognition for site information, findings information, treatment information, and hemostasis information. Note that, in a case where there are a plurality of lesions or the like, a series of processing (acceptance of audio input triggers, setting audio recognition dictionaries, and audio recognition in a cycle from imaging start to hemostasis) can be repeated for each lesion or the like.

[Audio Recognition and Words Displayed as Results]

In the endoscope system 10, in the audio recognition, the audio recognition unit 62B and the display control unit 65 (processor) can recognize only the registered words that are registered in the set audio recognition dictionary, and display (output) the result of the audio recognition for the registered word on the display device 70 (output device, display device) (adaptive audio recognition). According to this form, only the registered words registered in the set audio recognition dictionary are audio-recognized, so that the recognition accuracy can be improved. Note that, in such adaptive audio recognition, the registered words of the audio recognition dictionary may be set so that the wake word is not recognized, or the registered words may be set to include the wake word.

In addition, in the endoscope system 10, in the audio recognition, the audio recognition unit 62B and the display control unit 65 (processor) can recognize the registered words that are registered in the set audio recognition dictionary and specific words, and display (output) the result of the audio recognition for the registered word among the recognized words on the display device 70 (output device, display device) (non-adaptive audio recognition). Note that an example of the "specific word" is a wake word for the audio input device, but the "specific word" is not limited thereto.

Note that, in the endoscope system 10, which of the above forms (adaptive audio recognition, non-adaptive audio recognition) is used to perform audio recognition and to display the result can be set on the basis of an instruction input from the user via the input device 50, the operation part 22, or the like.

[Notification to User Using Switching Display of Icon]

Note that, in the endoscope system 10, it is preferable that the display control unit 65 (processor) notifies the user that the audio recognition dictionary is set (the fact that the audio recognition dictionary is set and which dictionary is set) and that the audio recognition is possible. As illustrated in FIGS. 13A to 13D, the display control unit 65 can perform notification by switching icons displayed on the screen. In the examples illustrated in FIGS. 13A to 13D, the display control unit 65 displays the icon indicating the image recognizer that is operating (or displaying the recognition result on the screen) among the respective units of the image recognition processing unit 63 on the screen such as the screen 70A, and switches the display to a microphone icon in a case where the image recognizer recognizes the specific subject (audio input trigger) and an audio recognition period is reached, thereby notifying the user (refer to FIGS. 8, 16A, 17, and 18).

Figure 13A:
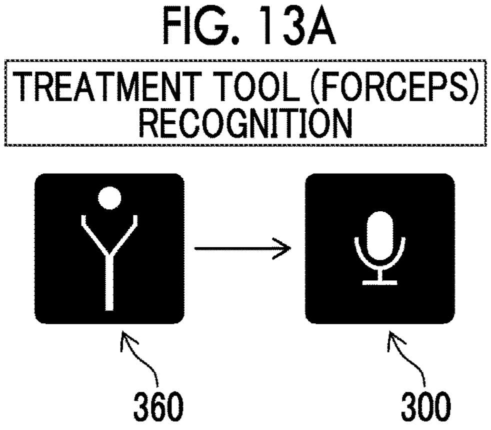
FIGS. 13A to 13D are diagrams illustrating states of notification using a screen display of an icon.
Figure 13B:
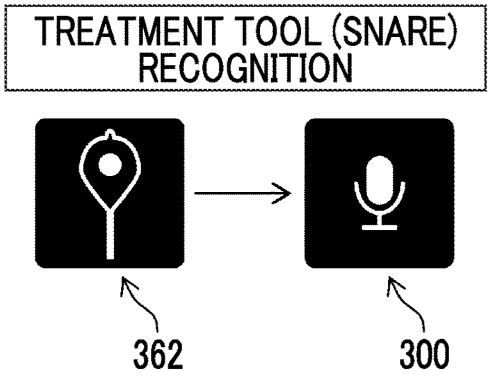
Figure 13C:
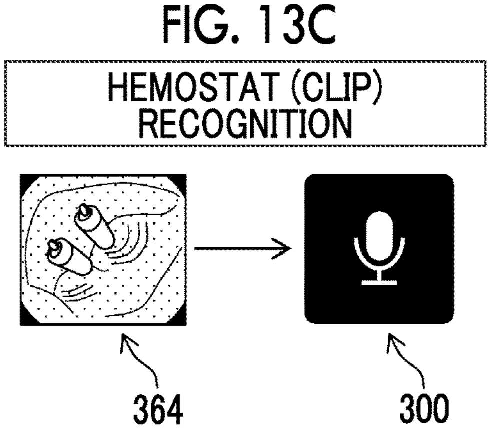
Figure 13D:
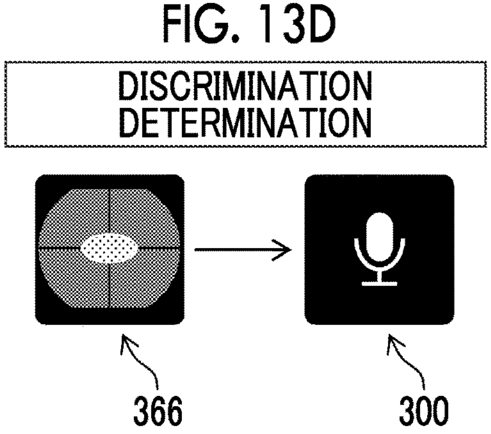

Specifically, FIGS. 13A and 13B illustrate a state where the treatment tool detection unit 63D is operating, but the specific subjects as the recognition target are different (forceps, snare). Therefore, the display control unit 65 displays different icons 360 and 362, and switches to the microphone icon 300 in a case where the forceps or the snare is actually recognized, thereby notifying the user that the audio recognition is possible. Similarly, FIGS. 13C and 13D illustrate states in which the hemostat detection unit 63E and the discrimination unit 63B are operating, respectively. The display control unit 65 displays an icon 364 or an icon 366, and switches to the microphone icon 300 in a case where the hemostat or the lesion is recognized, thereby notifying the user that the audio recognition is possible.

Through such notification, the user can easily ascertain that a specific image recognizer is operating and that a period in which audio recognition is possible is reached. Note that the display control unit 65 may display and switch the icon according to not only the operation situation of each unit of the image recognition processing unit 63 but also an operation situation and an input situation of the microphone 51 and/or the foot switch 52.

[Execution of Audio Recognition During Specific Period]

The audio recognition unit 62B (processor) can execute the audio recognition using the set audio recognition dictionary during a specific period after the setting (period in which predetermined conditions are satisfied). "Predetermined conditions" may be the output of the recognition results from the image recognizer, may be conditions regarding the output contents, or may specify an execution time itself of the audio recognition (three seconds, five seconds, or the like). In a case of specifying the execution time, it is possible to specify an elapsed time from the dictionary setting, or an elapsed time after the user is notified that the audio input is possible.

Figure 14:
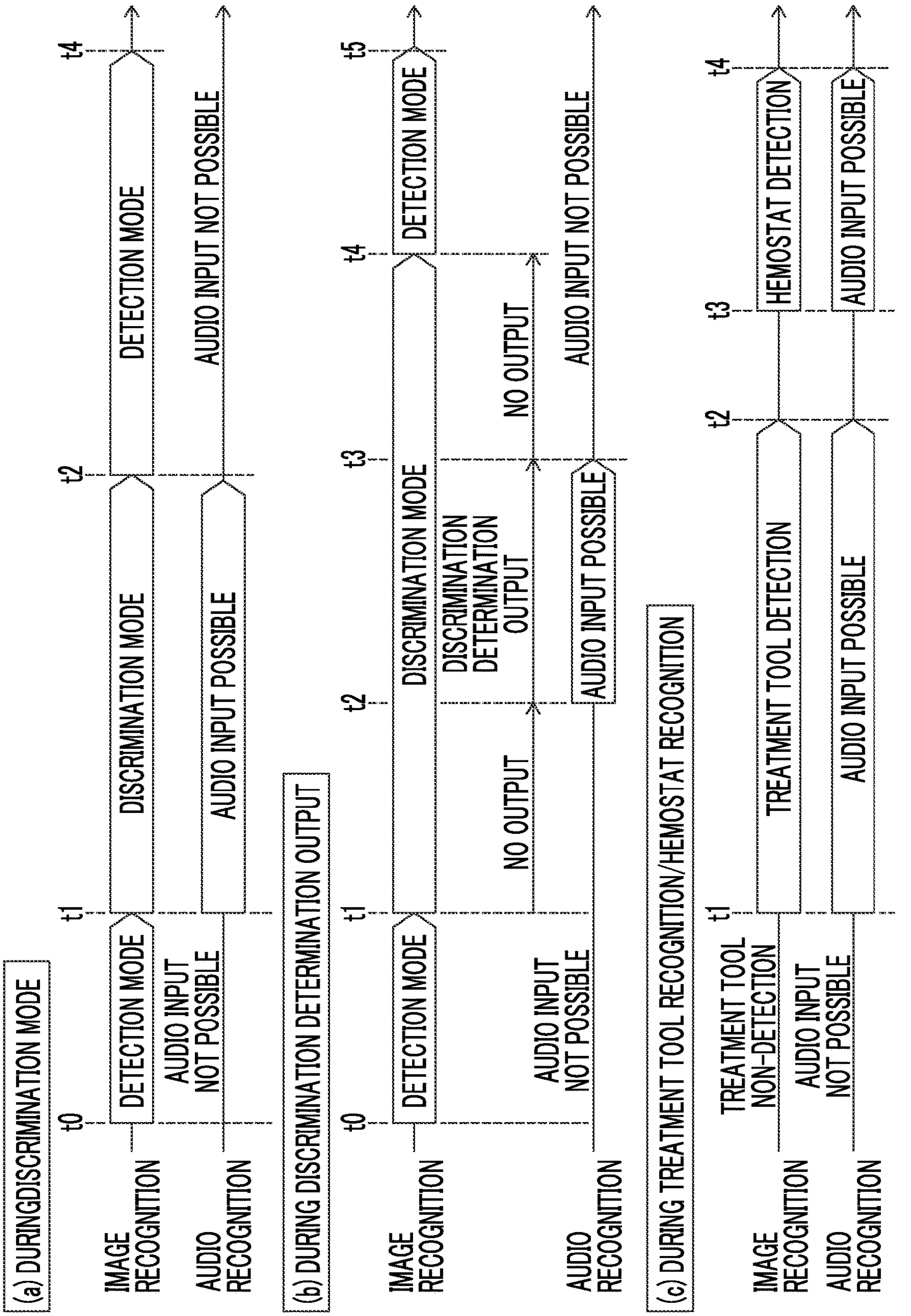
FIG. 14 is a diagram illustrating a state of executing an audio input during a specific period.

FIG. 14 is a diagram illustrating a state of executing the audio recognition during a specific period. In the example illustrated in the (a) part of FIG. 14, the audio recognition unit 62B performs the audio recognition only during the period in the discrimination mode (period in which the discrimination unit 63B is operating; time point t1 to time point t2). In addition, in the example illustrated in the (b) part of FIG. 14, the audio recognition unit 62B performs the audio recognition only during the period in which the discrimination unit 63B outputs the discrimination result (discrimination determination result) (time point t2 to time point t3). As described above, the discrimination unit 63B can be configured to perform the output in a case where the reliability degree of the discrimination result or the statistical value thereof is equal to or greater than the threshold value. In addition, in the example illustrated in the (c) part of FIG. 14, the audio recognition unit 62B performs the audio recognition only during the period in which the treatment tool detection unit 63D detects the treatment tool (time point t1 to time point t2) and the period in which the hemostat detection unit 63E detects the hemostat (time point t3 to time point t4). Note that, in FIGS. 14 and 15, the acceptance of the audio input trigger and the setting of the audio recognition dictionary are not illustrated.

In this manner, by executing the audio recognition during a specific period, it is possible to reduce the risk of unnecessary recognition or erroneous recognition, and to perform the examination smoothly.

Note that the audio recognition unit 62B may set the period of the audio recognition for each image recognizer, or may set the period of the audio recognition depending on the type of the audio input trigger. In addition, the audio recognition unit 62B may set "predetermined conditions" and "execution time of the audio recognition" on the basis of an instruction input from the user via the input device 50, the operation part 22, or the like.

[Audio Recognition After Manual Operation]

Figure 15:
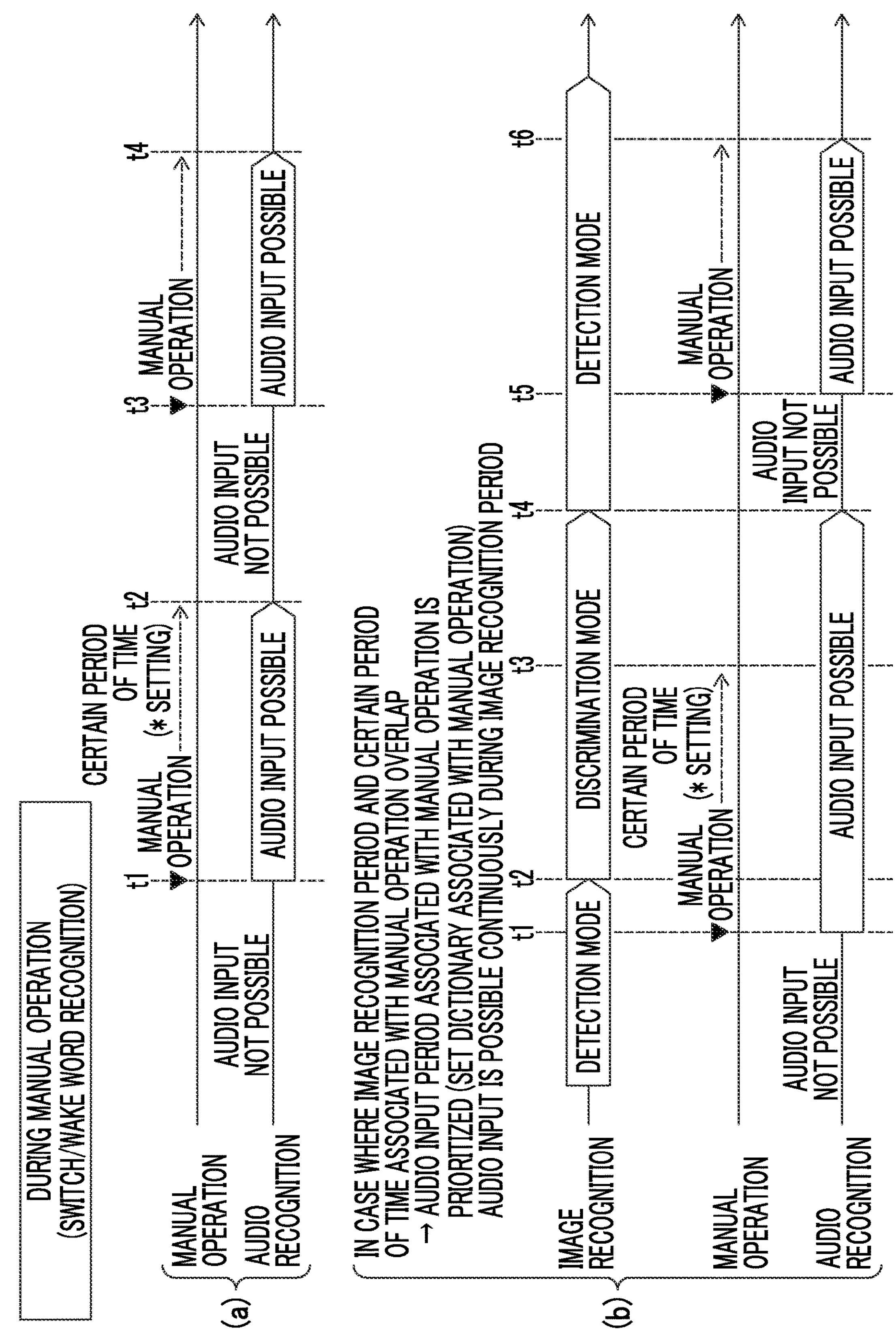
FIG. 15 is another diagram illustrating a state of executing an audio input during a specific period.

FIG. 15 is another diagram illustrating a state of executing the audio recognition during a specific period. The (a) part of FIG. 15 illustrates an example of setting the audio recognition dictionary and executing the audio recognition for a certain period of time (time point t1 to time point t2 and time point t3 to time point t4 in the (a) part of FIG. 15) after a manual operation. The audio recognition unit 62B can perform the audio recognition using the user's operation on the input device 50, the operation part 22, or the like as the "manual operation". Specifically, the "manual operation" may be an operation on various operation devices described above, an input of the wake word via the microphone 51, an operation on the foot switch 52, an imaging instruction of the endoscopic image (video, static image), a switching operation from a detection mode (state in which the lesion part detection unit 63A outputs the result) to a discrimination mode (state in which the discrimination unit 63B outputs the result), or an operation on the operation device connected to the endoscope system 10.

In addition, the (b) part of FIG. 15 illustrates an example of processing in a case where the period of the audio recognition based on the image recognition and the "certain period of time after the manual operation" described above overlap. Specifically, from time point t1 to time point t3, the audio recognition unit 62B prioritizes the audio recognition associated with the manual operation over the audio recognition according to the discrimination result output from the discrimination unit 63B, sets the audio recognition dictionary based on the manual operation, and performs the audio recognition.

In a case where the audio recognition based on the manual operation is prioritized in this manner, the period of the audio recognition based on the image recognition may be continuous with the period of the audio recognition associated with the manual operation. For example, in the example illustrated in the (b) part of FIG. 15, the audio recognition unit 62B sets the audio recognition dictionary based on the discrimination result of the discrimination unit 63B, and performs the audio recognition from time point t3 to time point t4 following the audio recognition period (time point t1 to time point t2) based on the manual operation. Meanwhile, from time point t4 to time point t5, since the audio recognition period based on the manual operation ends, the audio recognition unit 62B does not set the audio recognition dictionary, and does not perform the audio recognition. Similarly, the audio recognition unit 62B sets the audio recognition dictionary based on the manual operation, and performs the audio recognition from time point t5 to time point t6, and after time point t6 at which the audio recognition period ends, the audio recognition unit 62B does not perform the audio recognition.

[Screen Display of Remaining Time]

Figure 16A:
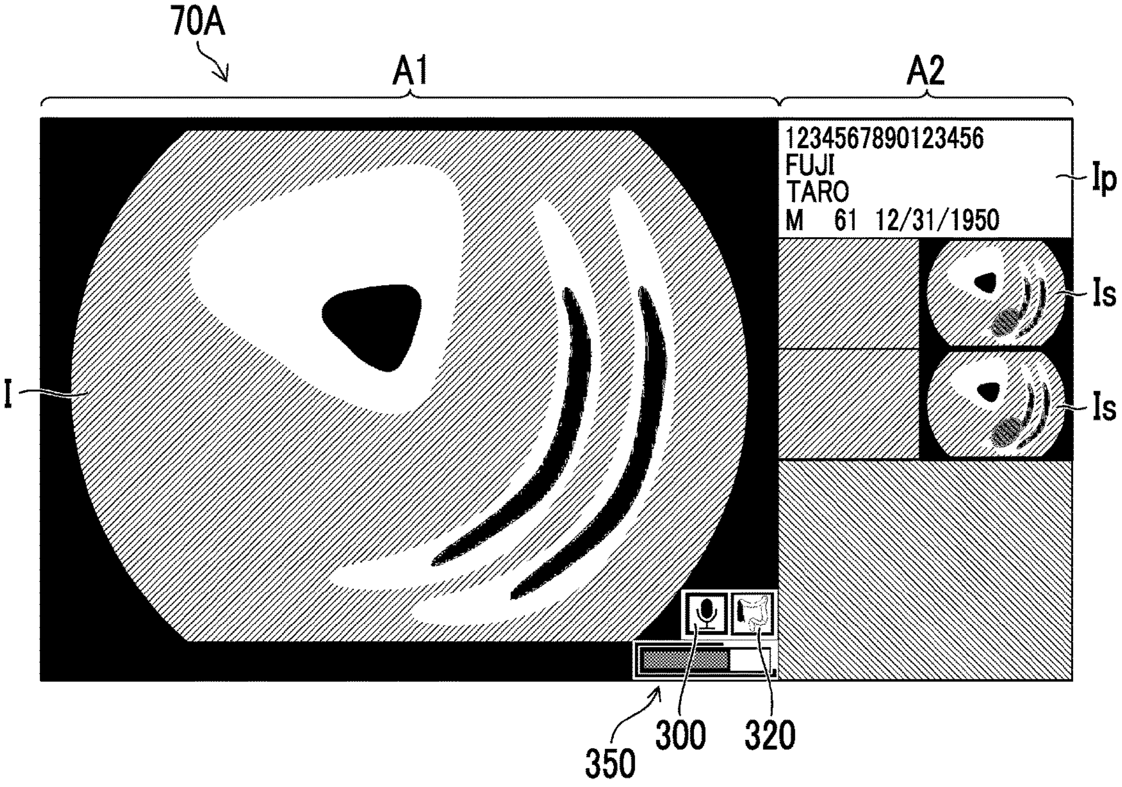
FIGS. 16A and 16B are diagrams illustrating examples of a screen display of a remaining time of an audio recognition period.
Figure 16B:
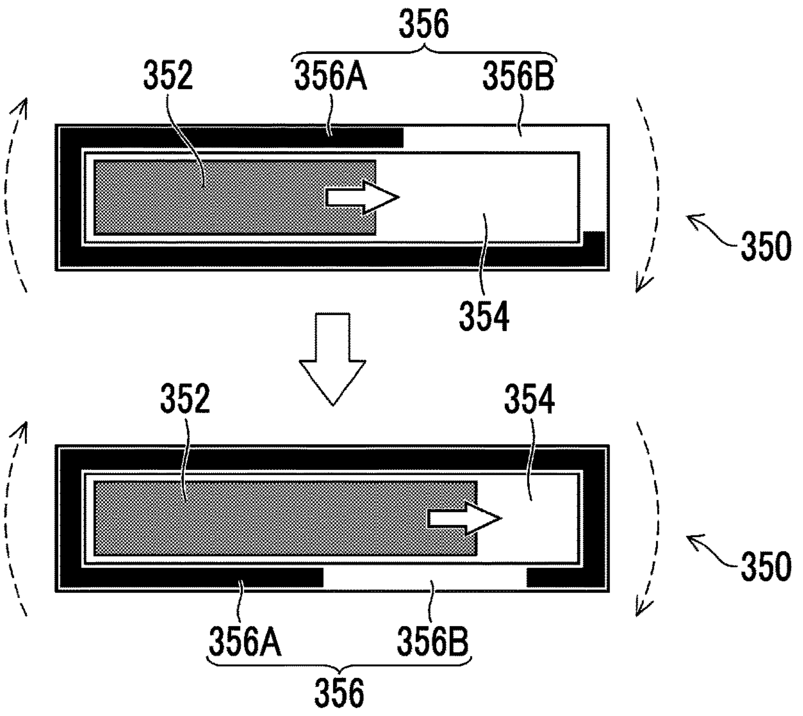

The audio recognition unit 62B and the display control unit 65 may display the remaining time of the audio recognition period on the screen of the display device 70. That is, the audio recognition unit 62B and the display control unit 65 may perform the audio recognition during a predetermined period after the audio recognition dictionary is set. FIGS. 16A and 16B are diagrams illustrating examples of the screen display of the remaining time. FIG. 16A is an example of the display on the screen 70A, and a remaining time meter 350 is displayed. In addition, FIG. 16B is an enlarged diagram of the remaining time meter 350. In the remaining time meter 350, a hatched region 352 is lengthened as the time elapses, and a plain region 354 is shortened as the time elapses. In addition, a frame 356 consisting of a black background region 356A and a white background region 356B rotates around these regions to call the user's attention. The audio recognition unit 62B and the display control unit 65 may rotate and display the frame 356 in a case where it is detected the audio is input.

Note that the audio recognition unit 62B and the display control unit 65 may set different periods depending on the audio input trigger and the audio recognition dictionary, as the period in which the audio recognition is performed. In addition, the period may be set according to the user's operation via the input device 50.

Note that the audio recognition unit 62B and the display control unit 65 may output the remaining time using numbers or audio. Note that the remaining time is zero in a case where the screen display of the microphone icon 300 (refer to FIGS. 8, 16A, 17, and 18) disappears.

[Display of Audio Recognition Candidate/Selection Result]

Figure 17:
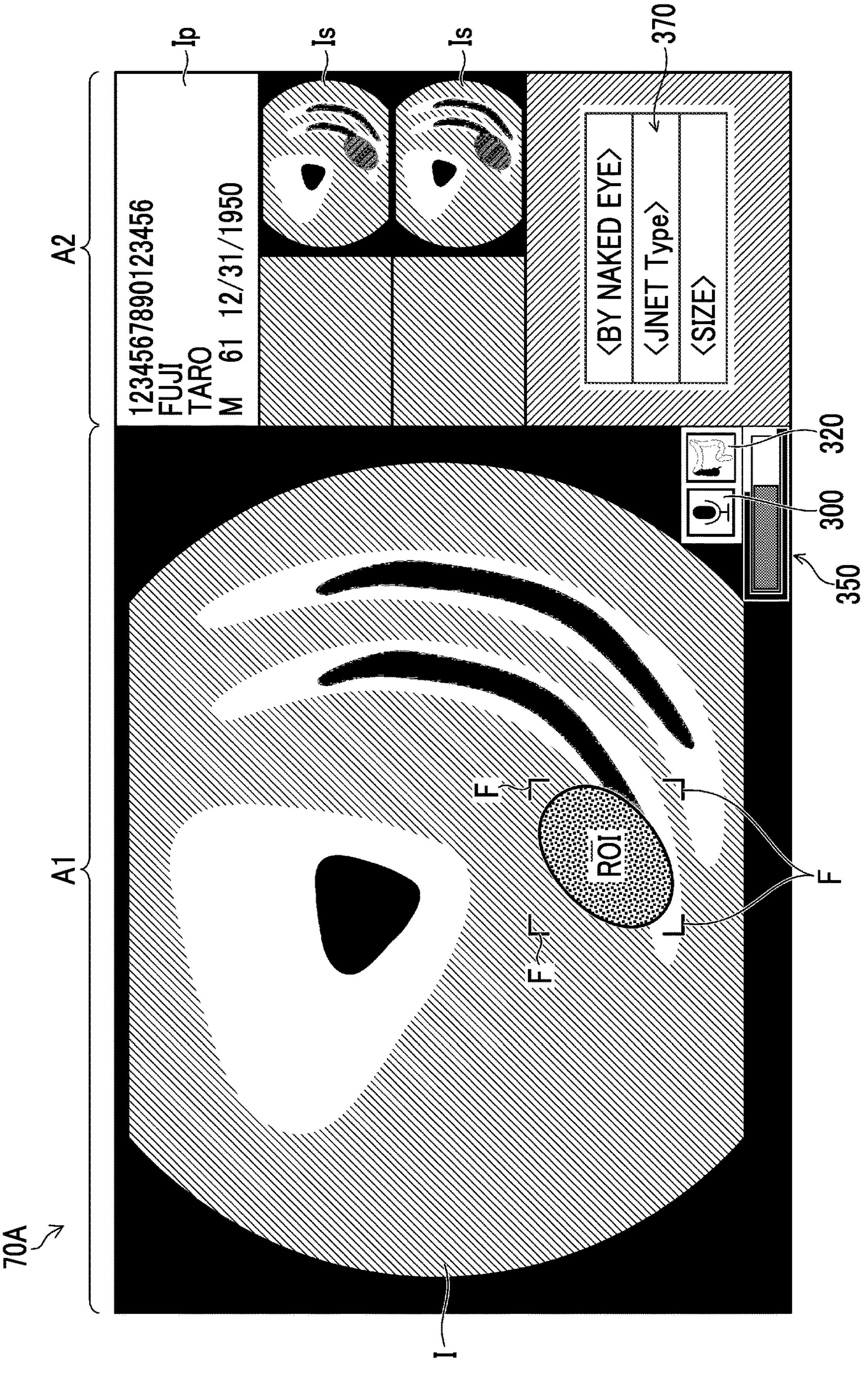
FIG. 17 is a diagram illustrating an example of a screen display of candidates for audio recognition.

The audio recognition unit 62B and the display control unit 65 may display the candidates for the audio recognition on the screen, and may allow the user to select the candidate. In addition, the audio recognition result may be displayed on the screen of the display device 70. FIG. 17 is a diagram illustrating an example of a screen display of candidates for the audio recognition and the audio recognition result (a region of interest ROI and a frame F are also displayed in FIG. 17). FIG. 17 illustrates a state in which the discrimination unit 63B outputs the discrimination result, and the contents of the audio recognition dictionary "findings set A" (refer to FIG. 10A) corresponding to the output of the discrimination result are displayed in a region 370 on the screen 70A. The audio recognition unit 62B can confirm a conversion (word selection) according to the selection operation of the user via the microphone 51, the foot switch 52, or other operation devices. Note that the audio recognition unit 62B and the display control unit 65 can use the input of the audio input trigger or the setting of the audio recognition dictionary as the trigger for the candidate display.

Figure 18:
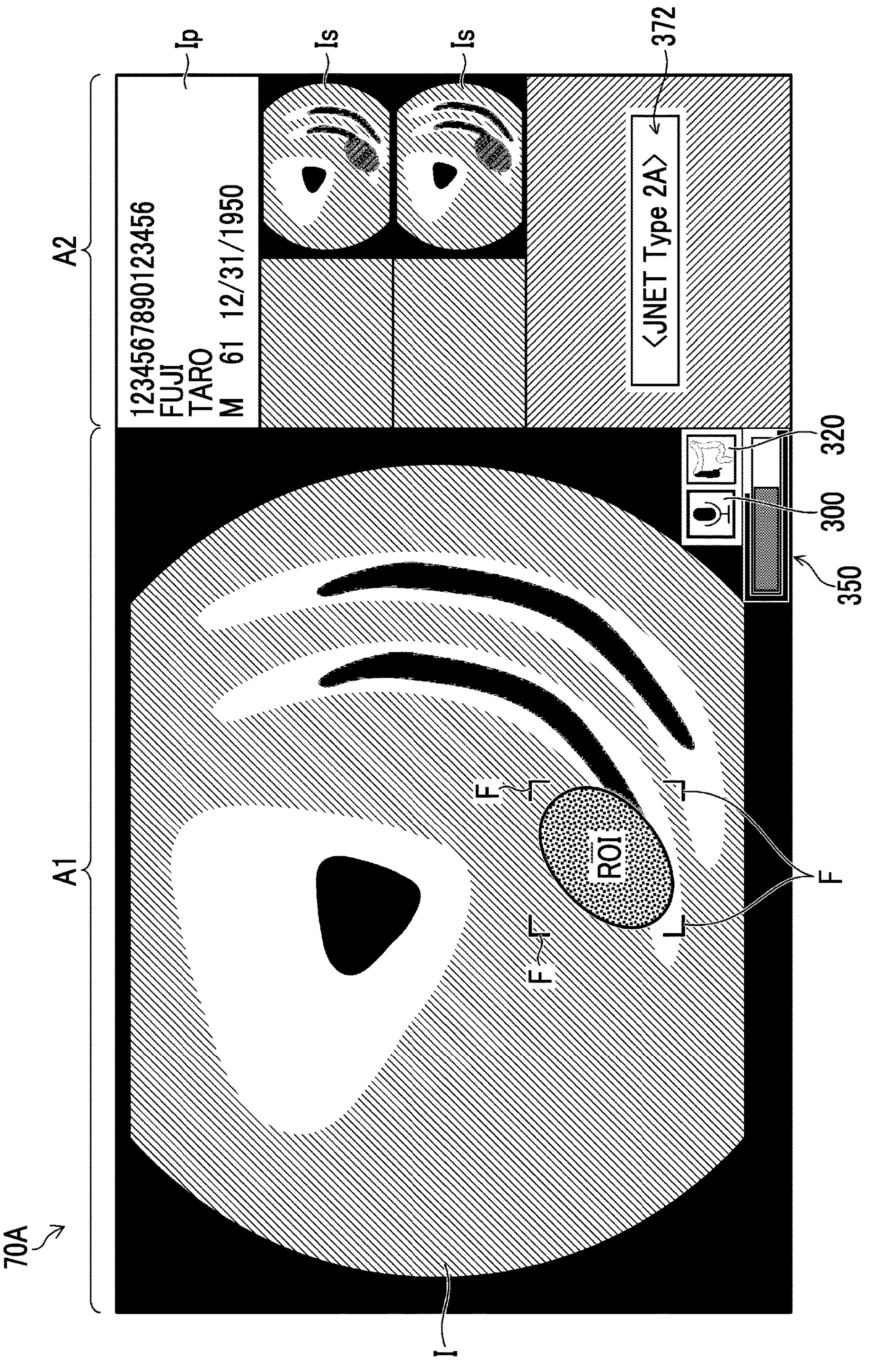
FIG. 18 is a diagram illustrating an example of a screen display of an audio recognition result.

FIG. 18 is a diagram illustrating an example of a screen display of the audio recognition result. As illustrated in FIG.

18, the display control unit 65 can display the word ("JNET TYPE 2A" in the example of FIG. 18) selected by the user on the screen (region 372).

[Variation of Display of Audio Recognition Result]

In the present invention, a display mode of the audio recognition result is not limited to the mode illustrated in the example of FIG. 18 or the like. In addition to the aspects described above, the audio recognition unit 62B and the display control unit 65 may display the result of the audio recognition in text in real time in the display region 340 (refer to FIG. 8) or the like, and then display the confirmed results in the region 372 as illustrated in FIG. 18. In addition, the audio recognition unit 62B and the display control unit 65 may display the selected or confirmed result of the audio recognition in a superimposed manner in the display region of the video (for example, the endoscopic image I illustrated in FIGS. 8 and 18) (in the example illustrated in FIG. 18, "JNET TYPE 2A" can be displayed near the region of interest ROI or the frame F).

The audio recognition unit 62B and the display control unit 65 may set a display position of the selection result or the confirmation result of the audio recognition according to the audio recognition result, the type of the recognized subject, or the like. For example, the audio recognition unit 62B and the display control unit 65 can display the audio recognition result for "findings" near the region of interest of the video (for example, the region of interest ROI of FIG. 18) in a superimposed manner, and display the audio recognition results for "treatment" and "hemostasis" in a region other than the display region of the video (for example, near the icon 300, the icon 320, or the remaining time meter 350).

[Switching Audio Recognition Dictionary According to Quality of Image Recognition]

In the audio recognition described above, the audio recognition unit 62B may switch the audio recognition dictionary 62C according to the quality of the image recognition executed by the image recognition processing unit 63 (refer to FIG. 7), as described below with reference to FIG. 19 (diagram illustrating a state of processing according to the quality of the image recognition).

In a case where the lesion candidate (specific subject) is included in the endoscopic image, the period in which the discrimination unit 63B outputs the discrimination result is the audio recognition period (same as in the (a) part of FIG. 14). In such a situation, as illustrated in the (a) part of FIG. 19, it is assumed that the observation quality (image quality of the endoscopic image) is poor from time point t1 to time point t2 (detection mode; the lesion part detection unit 63A outputs the result). Possible causes of the poor observation quality include, for example, inappropriate exposure or focusing conditions, or obstruction of a visual field due to residue.

Figure 19:
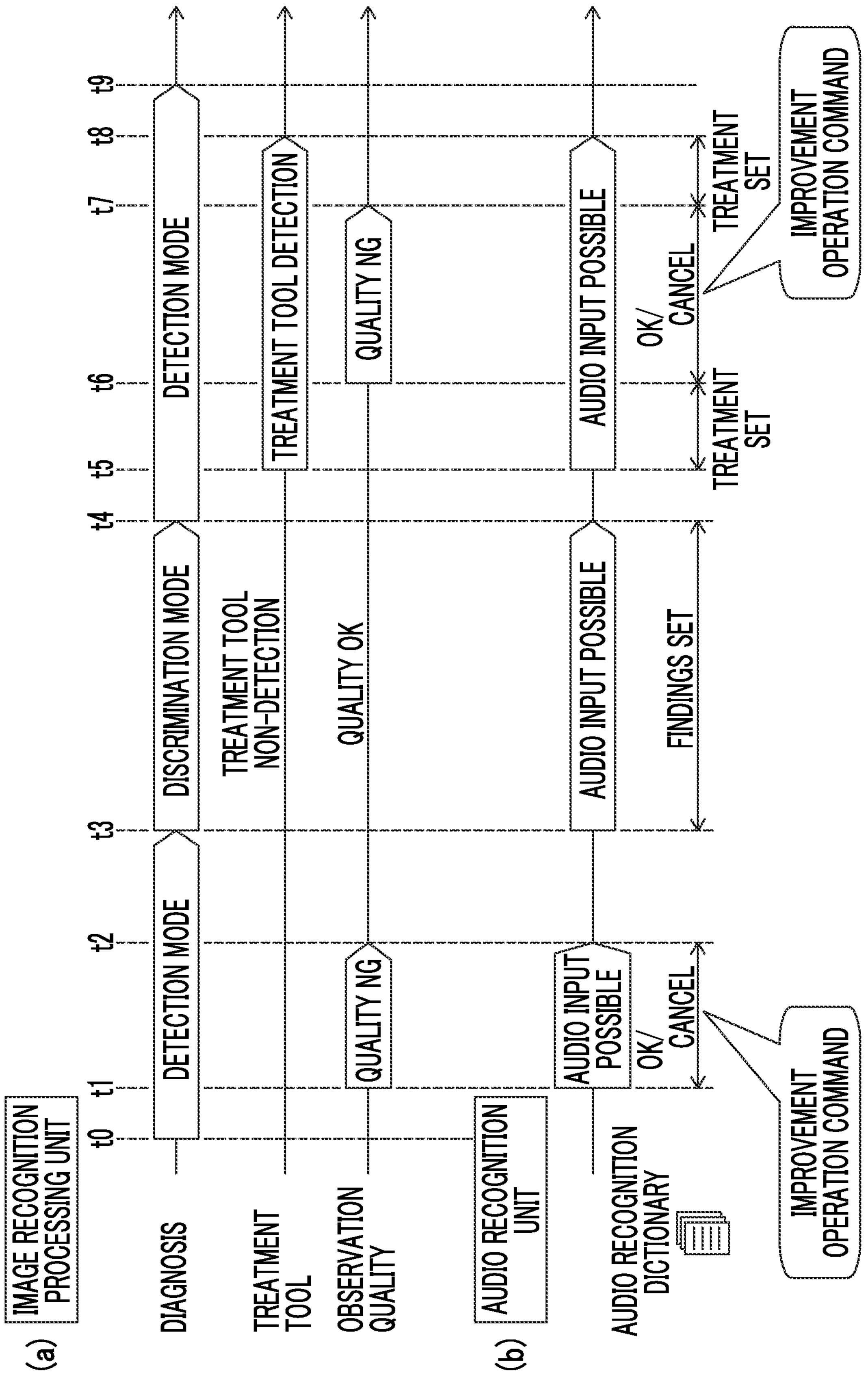
FIG. 19 is a diagram illustrating a state of processing according to a quality of image recognition.

In this case, as illustrated in the (b) part of FIG. 19, the audio recognition unit 62B performs the audio recognition from time point t1 to time point t2 at which the audio recognition would not normally be performed (in a case where the image quality is good), and accepts a command for an image quality improvement operation. The audio recognition unit 62B can set an "image quality improvement set" in which, for example, words such as "gas injection, lighting on, sensor sensitivity 'high'" are registered, as the audio recognition dictionary 62C, and perform the audio recognition.

From time point t3 to time point t4 (discrimination mode: the discrimination unit 63B outputs the result), the audio recognition unit 62B performs the audio recognition using the audio recognition dictionary "findings set" as usual.

In addition, from time point t4 to time point t9, since the mode is the detection mode, the audio recognition unit 62B does not normally perform the audio recognition, and from time point t5 to time point t8, since the treatment tool is detected, the audio recognition unit 62B sets a "treatment set" as the audio recognition dictionary 62C, and performs the audio recognition. However, from time point t6 to time point t7, it is assumed that the observation quality is poor. The audio recognition unit 62B can accept a command for an image quality improvement operation during this period (time point t6 to time point t7) similar to time point t1 to time point t2.

In this manner, in the endoscope system 10, it is possible to flexibly set the audio recognition dictionary according to the observation quality and to perform appropriate audio recognition.

[Record of Report Creation Support Information]

In a case where the audio recognition is performed, the examination information output control unit 66 (processor) can associate the endoscopic images (medical images in chronological order) with the results of the audio recognition, and record the endoscopic images and the results in the recording device such as the recording device 75, the storage unit of the medical information processing apparatus 80, and the endoscope information management system 100. The examination information output control unit 66 may associate the endoscopic image in which a specific subject is shown and the determination result (that the specific subject is shown in the image) of the image recognition, and record the endoscopic image and the determination result. The examination information output control unit 66 may perform recording according to the user's operation on the operation device, or may perform recording automatically without depending on the user's operation. With such recording, in the endoscope system 10, it is possible to support the user in creating an examination report.

[Other]

In the embodiments described above, a case has been described in which the present invention is applied to the endoscope system for a lower digestive tract, but the present invention can also be applied to an endoscope for an upper digestive tract.

The embodiments of the present invention have been described above, but the invention is not limited to the above-described aspects and can have various modifications without departing from the scope of the invention.

EXPLANATION OF REFERENCES

1: endoscopic image diagnosis support system
10: endoscope system
20: endoscope
21: insertion part
21A: distal end portion
21B: bendable portion
21C: soft portion
21*a*: observation window
21*b*: illumination window
21*c*: air/water supply nozzle
21*d*: forceps outlet
22: operation part
22A: angle knob
22B: air/water supply button
22C: suction button
22D: forceps insertion port
23: connection part
23A: cord

23B: light guide connector
23C: video connector
30: light source device
40: endoscopic image generation device
41: endoscope control unit
42: light source control unit
43: image generation unit
44: input control unit
45: output control unit
50: input device
51: microphone
52: foot switch
60: endoscopic image processing device
61: endoscopic image acquisition unit
62: input information acquisition unit
62A: information acquisition unit
62B: audio recognition unit
62C: audio recognition dictionary
63: image recognition processing unit
63A: lesion part detection unit
63B: discrimination unit
63C: specific region detection unit
63D: treatment tool detection unit
63E: hemostat detection unit
63F: measurement unit
64: audio input trigger acceptance unit
65: display control unit
66: examination information output control unit
70: display device
70A: screen
75: recording device
80: medical information processing apparatus
100: endoscope information management system
200: user terminal
300: icon
320: icon
340: display region
350: remaining time meter
352: region
354: region
356: frame
356A: black background region
356B: white background region
360: icon
362: icon
364: icon
366: icon
370: region
372: region
A1: main display region
A2: secondary display region
F: frame
I: endoscopic image
Ip: information
Is: static image
ROI: region of interest

What is claimed is:

1. An endoscope system comprising:
an audio input device;
an image sensor that images a subject; and
a processor,
wherein the processor is configured to:
acquire a plurality of medical images obtained by the image sensor imaging the subject in chronological order;
perform image recognition on the acquired plurality of medical images a plurality of times using a plurality of image recognizers respectively corresponding a plurality of types of specific subjects;
detect, using the image recognition, whether at least one type of specific subject of the plurality of types of specific subjects is included in the plurality of medical images, and accept a determination result indicating that the specific subject is included, as an audio input trigger;
set, when the audio input trigger is input, an audio recognition dictionary corresponding to the type of the specific subject determined to be included in the plurality of medical images; and
perform audio recognition on audio input to the audio input device after the setting, using the set audio recognition dictionary.

2. The endoscope system according to claim 1,
wherein the processor is configured to:
detect at least one lesion as one of the specific subjects;
further perform, in a case where the at least one lesion is detected from the plurality of medical images, discrimination processing on the detected at least one lesion using image recognition; and
set, in a case where a result of discrimination is obtained, a predetermined specific audio recognition dictionary.

3. The endoscope system according to claim 1,
wherein, in a case where any one of an imaging start instruction of the plurality of medical images, an operation to an operation device connected to the endoscope system and an input of a wake word for the audio input device, is performed, the processor sets a predetermined specific audio recognition dictionary.

4. The endoscope system according to claim 3,
wherein, in a case where the imaging start instruction of the plurality of medical images is performed, the processor sets an audio recognition dictionary according to the imaging start instruction.

5. The endoscope system according to claim 3,
wherein, in a case where the operation to the operation device connected to the endoscope system is performed, the processor sets an audio recognition dictionary according to the operation.

6. The endoscope system according to claim 3,
wherein, in a case where the input of the wake word for the audio input device is performed, the processor sets an audio recognition dictionary according to contents of the wake word.

7. The endoscope system according to claim 1,
the processor performs the image recognition for each of the specific subjects to be recognized.

8. The endoscope system according to claim 1,
wherein, in the audio recognition, the processor recognizes only registered words that are registered in the set audio recognition dictionary, and causes an output device to output a result of the audio recognition for the registered words.

9. The endoscope system according to claim 1,
wherein, in the audio recognition, the processor recognizes registered words that are registered in the set audio recognition dictionary and specific words, and causes an output device to output a result of the audio recognition for the registered words among the recognized words.

10. The endoscope system according to claim 1,
wherein the processor performs the image recognition using the plurality of image recognizers configured by machine learning.

11. The endoscope system according to claim 1, wherein the processor records the medical image decided to include the specific subject, among the plurality of medical images, the determination result using the image recognition for the specific subject, and a result of the audio recognition in a recording device in association with each other.

12. The endoscope system according to claim 1, wherein the processor decides at least one of a lesion, a lesion candidate region, a landmark, a treated region, a treatment tool, or a hemostat, as the specific subject.

13. The endoscope system according to claim 1, wherein the processor executes the audio recognition using the set audio recognition dictionary during a period in which a predetermined condition is satisfied after the setting.

14. The endoscope system according to claim 13, wherein the processor sets the period for each of the plurality of image recognizers that performs the image recognition.

15. The endoscope system according to claim 13, wherein the processor displays a remaining time of the period on a screen of a display device.

16. The endoscope system according to claim 1, wherein the processor performs the audio recognition for site information, findings information, treatment information, and hemostasis information.

17. The endoscope system according to claim 1, wherein the processor displays a result of the audio recognition on a display device.

18. A medical information processing apparatus comprising:

a processor configured to:

acquire a plurality of medical images obtained by an image sensor imaging a subject in chronological order;

perform image recognition on the acquired plurality of medical images a plurality of times using a plurality of image recognizers respectively corresponding a plurality of types of specific subjects;

detect, using the image recognition, whether at least one type of specific subject of the plurality of types of specific subjects is included in the plurality of medical images, and accept a determination result indicating that the specific subject is included, as an audio input trigger;

set, when the audio input trigger is input, an audio recognition dictionary corresponding to the type of the specific subject determined to be included in the plurality of medical images; and perform audio recognition on audio input to the audio input device after the setting, using the set audio recognition dictionary.

19. A medical information processing method executed by an endoscope system including an audio input device, an image sensor that images a subject, and a processor, the medical information processing method comprising:

acquiring, by the processor, a plurality of medical images obtained by the image sensor imaging the subject in chronological order;

performing, by the processor, image recognition on the acquired plurality of medical images a plurality of times using a plurality of image recognizers respectively corresponding a plurality of types of specific subjects;

detecting, using the image recognition, whether at least one type of specific subject of the plurality of types of specific subjects is included in the plurality of medical images, and accepting a determination result indicating that the specific subject is included, as an audio input trigger;

setting, by the processor, when the audio input trigger is input, an audio recognition dictionary corresponding to the type of the specific subject determined to be included in the plurality of medical images; and performing, by the processor, audio recognition on audio input to the audio input device after the setting, using the set audio recognition dictionary.

20. A non-transitory, tangible recording medium which records thereon a computer readable code of a program for causing a processor of an endoscope system including an audio input device and an image sensor that images a subject, to implement functions comprising:

acquiring a plurality of medical images obtained by the image sensor imaging the subject in chronological order;

performing image recognition on the acquired plurality of medical images a plurality of times using a plurality of image recognizers respectively corresponding a plurality of types of specific subjects;

detecting, using the image recognition, whether at least one type of specific subject of the plurality of types of specific subjects is included in the plurality of medical images, and accepting a determination result indicating that the specific subject is included, as an audio input trigger;

setting, when the audio input trigger is input, an audio recognition dictionary corresponding to the type of the specific subject determined to be included in the plurality of medical images; and performing audio recognition on audio input to the audio input device after the setting, using the set audio recognition dictionary.

* * * * *